United States Patent
Olson

(10) Patent No.: US 9,734,284 B2
(45) Date of Patent: Aug. 15, 2017

(54) HARDWARE ACCELERATION OF SHORT READ MAPPING FOR GENOMIC AND OTHER TYPES OF ANALYSES

(71) Applicant: Pico Computing, Inc., Seattle, WA (US)

(72) Inventor: Corey B. Olson, Madison, WI (US)

(73) Assignee: Micron Technology, Inc., Boise, ID (US)

( * ) Notice: Subject to any disclaimer, the term of this patent is extended or adjusted under 35 U.S.C. 154(b) by 181 days.

(21) Appl. No.: 14/201,824

(22) Filed: Mar. 8, 2014

(65) Prior Publication Data

US 2014/0297196 A1 Oct. 2, 2014

Related U.S. Application Data

(60) Provisional application No. 61/790,407, filed on Mar. 15, 2013, provisional application No. 61/790,720, filed on Mar. 15, 2013, provisional application No. 61/940,009, filed on Feb. 14, 2014, provisional application No. 61/940,472, filed on Feb. 16, 2014.

(51) Int. Cl.
*G06F 19/22* (2011.01)
(52) U.S. Cl.
CPC .................................. *G06F 19/22* (2013.01)
(58) Field of Classification Search
None
See application file for complete search history.

(56) References Cited

PUBLICATIONS

Tom White, "Hadoop: The definitive guide", O'Reilly Media, May 2009.*
Peter Alfke XAPP 091 Nov. 24, 1997.*
Mueller et al. VLDB Aug. 24, 2009.*
Matthew M. Hosier at www.ee.washington.edu/faculty/.../mhosler.pdf Oct. 14, 1997.*

* cited by examiner

*Primary Examiner* — Joseph Woitach
(74) *Attorney, Agent, or Firm* — Nancy R. Gamburd; Gamburd Law Group LLC

(57) ABSTRACT

A scalable FPGA-based solution to the short read mapping problem in DNA sequencing is disclosed which greatly accelerates the task of aligning short length reads to a known reference genome. A representative system comprises one or more memory circuits storing a plurality of short reads and a reference genome sequence; and one or more field programmable gate arrays configured to select a short read; to extract a plurality of seeds from the short read, each seed comprising a genetic subsequence of the short read; for each seed, to determine at least one candidate alignment location (CAL) in the reference genome sequence to form a plurality of CALs; for each CAL, to determine a likelihood of the short read matching the reference genome sequence in the vicinity of the CAL; and to select one or more CALs having the currently greater likelihood of the short read matching the reference genome sequence.

21 Claims, 15 Drawing Sheets

FIG. 18

|  | - | A | G | T | A | C | T | G | C | G | A |
|---|---|---|---|---|---|---|---|---|---|---|---|
| - | 0 | 0 | 0 | 0 | 0 | 0 | 0 | 0 | 0 | 0 | 0 |
| A | -2 | 2 | -2 | -2 | 2 | -2 | -2 | -2 | -2 | -2 | 2 |
| C | -3 | 0 | 0 | -2 | 0 | 4 | 2 | 1 | 0 | -1 | 0 |
| T | -4 | -1 | -2 | 2 | 0 | 2 | 6 | 4 | 3 | 2 | 1 |
| G | -5 | -2 | 1 | 0 | 0 | 1 | 4 | 8 | 6 | 5 | 4 |
| A | -6 | -3 | -1 | -1 | 2 | 0 | 3 | 6 | 6 | 4 | 7 |
| C | -7 | -4 | -2 | -2 | 0 | 4 | 2 | 5 | 8 | 6 | 5 |

(Columns labeled REFERENCE; rows labeled READ)

HARDWARE ACCELERATION OF SHORT READ MAPPING FOR GENOMIC AND OTHER TYPES OF ANALYSES

CROSS-REFERENCE TO A RELATED APPLICATION

This application is a nonprovisional of and further claims priority under 35 U.S.C. Section 119 to U.S. Provisional Patent Application No. 61/790,407, filed Mar. 15, 2013, inventors Corey B. Olson, entitled "Hardware Acceleration of Short Read Mapping", which is commonly assigned herewith, the entire contents of which are incorporated herein by reference with the same full force and effect as if set forth in their entirety herein, and with priority claimed for all commonly disclosed subject matter.

This application also is a nonprovisional of and further claims priority under 35 U.S.C. Section 119 to U.S. Provisional Patent Application No. 61/790,720, filed Mar. 15, 2013, inventors Paul T. Draghicescu et al., entitled "Inexact Search Acceleration on FPGAs Using the Burrows-Wheeler Transform", which is commonly assigned herewith, the entire contents of which are incorporated herein by reference with the same full force and effect as if set forth in their entirety herein, and with priority claimed for all commonly disclosed subject matter.

This application also is a nonprovisional of and further claims priority under 35 U.S.C. Section 119 to U.S. Provisional Patent Application No. 61/940,009, filed Feb. 14, 2014, inventors Jeremy B. Chritz et al., entitled "High Speed, Parallel Configuration of Multiple Field Programmable Gate Arrays", which is commonly assigned herewith, the entire contents of which are incorporated herein by reference with the same full force and effect as if set forth in their entirety herein, and with priority claimed for all commonly disclosed subject matter.

This application also is a nonprovisional of and further claims priority under 35 U.S.C. Section 119 to U.S. Provisional Patent Application No. 61/940,472, filed Feb. 16, 2014, inventors Jeremy B. Chritz et al., entitled "System and Method for Independent, Direct and Parallel Communication Among Multiple Field Programmable Gate Arrays", which is commonly assigned herewith, the entire contents of which are incorporated herein by reference with the same full force and effect as if set forth in their entirety herein, and with priority claimed for all commonly disclosed subject matter.

FIELD OF THE INVENTION

The present invention relates generally to computing systems, and more specifically to the use of configurable logic circuits such as FPGAs to accelerate short read mapping for genomic and other types of analyses.

BACKGROUND

Genetic (DNA) sequencing is revolutionizing many aspects of biology and medicine, and creating an entirely new field of personalized medicine, particularly suited for analysis of cancers and determinations of corresponding treatment options. The cost of gene sequencing has dropped considerably, while new sequencing machines continue to increase the throughput of DNA sequencing, allowing sequencing technology to be applied to a wide variety of disparate fields.

In the process of genetic sequencing, genetic material is typically cleaved at numerous chromosomal locations into comparatively short DNA fragments, and the nucleotide sequence of these comparatively short DNA fragments is determined. The comparatively short DNA fragments are typically a few tens to hundreds of bases in length, and are referred to in the field as "short reads". Such sequencing can be performed rapidly and in parallel, e.g., on the order of tens of billions of bases per day from one sequencing machine, which is a scale of several times that of human genome (approximately 3 billion bases in length).

For most applications, a complete genetic sequence of an organism is not determined de novo. Rather, in most instances, for the organism in question, a "reference" genome sequence has already been determined and is known. As the short reads are typically derived from randomly fragmenting many copies of an individual sample genome of such an organism, typically the first step for data analysis is the ordering of all of these fragments to determine the overall gene sequence of the individual sample using the reference genome sequence effectively as a template, i.e., mapping these short read fragments to the reference genome sequence. In this analysis, a determination is made concerning the best location in the reference genome to which each short read maps, and is referred to as the short read mapping problem.

This short read mapping problem is technically challenging, both due to the volume of data and because sample sequences are generally not identical to the reference genome sequence, but as expected, will contain a wide variety of individual genetic variations. Due to the sheer volume of data, e.g., a billion short reads from a single sample, the speed or runtime of the data analysis is significant, with the data analysis now becoming the effective bottleneck in gene sequencing. In addition, successful sequencing should exhibit sensitivity to genetic variations, to successfully map sequences that are not completely identical to the reference, both because of technical errors in the sequencing and because of genetic differences between the subject and the reference genome.

Short read mapping has traditionally been performed by software tools running on a cluster of processors, such as:
1. Bowtie, Ben Langmead, Cole Trapnell, Mihai Pop, and Steven L. Salzberg, "Ultrafast and memory-efficient alignment of short DNA sequences to the human genome," *Genome Biology*, vol. 10, no. 3, p. R25, March 2009;
2. BWA, Heng Li and Richard Durbin, "Fast and accurate short read alingment with Burrows-Wheeler transform," *Bioinformatics*, vol. 25, no. 14, pp. 1754-1760, July 2009;
3. MAQ, Heng Li, Jue Ruan, and Richard Durbin, "Mapping short DNA sequencing reads and calling variants using mapping quality scores," *Genome Research*, vol. 18, no. 11, pp. 1851-1858, November 2008; and
4. BFAST, N. Homer, B. Merriman, and S. F. Nelson, "BFAST: An Alignment Tool for Large Scale Genome Resequencing," *PLoS ONE*, vol. 4, no. 11, p. e7767, November 2009.

As mentioned above, as the genetic sequencing of short reads has now become a highly automated and rapid process, providing sequencing in several (e.g., two) hours, these software analytical tools have now become the bottleneck in genetic sequencing analysis, which may require many hours to many days to generate the resulting aligned sequence (e.g., 7 to 56 hours for, respectively, Bowtie and BFAST).

Accordingly, a need remains for a system having both hardware and software co-design to provide for independent and parallel involvement of multiple configurable logic circuits such as field programmable gate arrays ("FPGAs") to rapidly accelerate such genomic or other analysis and significantly reduce the time required to sequence a DNA sample. Such a system should also provide for greater sensitivity and accuracy than the prior art software solutions. In addition, such supercomputing applications would be served advantageously by parallel involvement of multiple FPGAs capable of operating independently and without extensive host involvement. Such a system should further provide for significantly parallel and rapid data transfers with minimal host involvement, including to and from memory located anywhere within the system.

SUMMARY OF THE INVENTION

The exemplary or representative embodiments of the present invention provide numerous advantages. Representative embodiments provide up to several orders of magnitude improvement over the prior art genetic mapping, not only in vastly improved speed up in runtime, but greatly improved and tunable sensitivity, allowing more short reads to be mapped to the reference genome sequence. The representative systems further provide a considerably lower energy consumption. These improvements will therefore allow much more rapid genetic sequence analysis and application of such sequencing to entirely new areas of research.

In a representative embodiment, a method is disclosed for acceleration of short read mapping to a reference genome sequence for genomic analysis, with the method comprising: using a field programmable gate array, selecting a short read from a plurality of short reads, each short read comprising a sequence of a plurality of genetic bases; using the field programmable gate array, extracting a plurality of seeds from the short read, each seed comprising a genetic subsequence of the short read; using the field programmable gate array, for each seed of the plurality of seeds, determining at least one candidate alignment location in the reference genome sequence to form a plurality of candidate alignment locations; using the field programmable gate array, for each candidate alignment location of the plurality of candidate alignment locations, determining a likelihood of the short read matching the reference genome sequence in the vicinity of the candidate alignment location; and using the field programmable gate array, selecting one or more candidate alignment locations, of the plurality of candidate alignment locations, having the currently greater likelihoods of the short read matching the reference genome sequence.

In a representative embodiment, the step of determining at least one candidate alignment location may further comprise: using a selected seed of the plurality of seeds, accessing a reference genome index. In a representative embodiment, the method may also include partitioning the reference genome index over a plurality of memories to form a plurality of reference genome index partitions.

In various representative embodiments, the step of selecting one or more candidate alignment locations having the currently greater likelihood may further comprise: selecting one or more first candidate alignment locations having the currently greater one or more first likelihoods from a first partition of the plurality of reference genome index partitions; comparing the one or more first likelihoods with one or more second likelihoods of one or more second candidate alignment locations from a second partition of the plurality of reference genome index partitions; and selecting the one or more candidate alignment locations having the currently greater likelihoods of the one or more first and second likelihoods. The representative method may further comprise: transferring the one or more candidate alignment locations having the currently greater likelihoods for mapping of the short read using a next, third partition of the plurality of reference genome index partitions.

In a representative embodiment, the step of accessing the reference genome index may further comprise hashing the selected seed, and using the hashed seed to access the reference genome index. Also in a representative embodiment, the step of hashing the selected seed may further comprise: generating a forward sequence and a reverse complement sequence for the selected seed; determining which of the forward sequence or the reverse complement sequence is lexicographically smaller; hashing the lexicographically smaller sequence to produce a hash result; and using the hash result as the hashed seed to access the reference genome index.

In various representative embodiments, the reference genome index comprises a pointer table and a candidate alignment location table. Also in a representative embodiment, each entry of the pointer table comprises a first predetermined number of the most significant bits of a hashed seed sequence and a pointer to a corresponding part of the candidate alignment location table, and each entry of the candidate alignment location table comprises a second predetermined number of the least significant bits of a hashed seed sequence and a corresponding candidate alignment location. For such embodiments, the step of accessing the reference genome index may further comprise: using the first predetermined number of the most significant bits of the selected hashed seed, accessing the pointer table to obtain a corresponding pointer; and using the corresponding pointer and the second predetermined number of the least significant bits of the selected hashed seed, determining the candidate alignment location.

A representative method may also comprise creating the reference genome index. In such a representative embodiment, the method may further comprise: determining all <seed, location> tuples in the reference genome sequence to form a plurality of <seed, location> tuples; sorting and eliminating redundant tuples from the plurality of <seed, location> tuples; for each seed, generating a forward sequence and a reverse complement sequence and determining which of the forward sequence or the reverse complement sequence is lexicographically smaller; for each seed, hashing the lexicographically smaller sequence to produce a hash result; and for each seed, using the hash result as the hashed seed for the reference genome index. Also in a representative embodiment, the method may further comprise: creating a pointer table, each entry of the pointer table comprising a first predetermined number of the most significant bits of the selected hashed seed and a corresponding pointer; and creating a candidate alignment location table, each entry of the candidate alignment location table comprising a second predetermined number of the least significant bits of the selected hashed seed and a corresponding candidate alignment location.

A representative method may also comprise filtering the plurality of candidate alignment locations to eliminate any redundant candidate alignment locations. A representative method may also comprise performing the selection, extraction, and determination steps in parallel using a plurality of field programmable gate arrays.

Also in a representative embodiment, the step of determining the likelihood of the short read matching the reference genome sequence may further comprise: performing a Smith-Waterman string matching of the short read with the reference genome sequence. For example, the method may further comprise: instantiating (or configuring) a plurality of Smith-Waterman engines in the field programmable gate array.

Also in a representative embodiment, the step of determining a likelihood of the short read matching the reference genome sequence in the vicinity of the candidate alignment location may further comprise: determining the vicinity of the candidate alignment location as a sequence beginning at the start of the candidate alignment location minus a predetermined offset and extending through the end of the candidate alignment location plus a length of the selected short read and the predetermined offset.

Representative systems for acceleration of short read mapping to a reference genome sequence for genomic analysis are also disclosed. A representative system embodiment comprises: one or more memory circuits storing a plurality of short reads and a reference genome sequence, each short read comprising a sequence of a plurality of genetic bases; and one or more field programmable gate arrays coupled to the one or more memory circuits, the one or more field programmable gate arrays configured to select a short read from the plurality of short reads; to extract a plurality of seeds from the short read, each seed comprising a genetic subsequence of the short read; for each seed of the plurality of seeds, to determine at least one candidate alignment location in the reference genome sequence to form a plurality of candidate alignment locations; for each candidate alignment location of the plurality of candidate alignment locations, to determine a likelihood of the short read matching the reference genome sequence in the vicinity of the candidate alignment location; and to select one or more candidate alignment locations, of the plurality of candidate alignment locations, having the currently greater likelihoods of the short read matching the reference genome sequence.

In a representative embodiment, the one or more field programmable gate arrays are further configured to use a selected seed, of the plurality of seeds, to access a reference genome index to determine the at least one candidate alignment location. Also in a representative embodiment, the reference genome index is partitioned over the one or more memory circuits to form a plurality of reference genome index partitions. In a representative embodiment. the one or more field programmable gate arrays are further configured to select one or more first candidate alignment locations having the currently greater one or more first likelihoods from a first partition of the plurality of reference genome index partitions; to compare the one or more first likelihoods with one or more second likelihoods of one or more second candidate alignment locations from a second partition of the plurality of reference genome index partitions; and to select the one or more candidate alignment locations having the currently greater likelihoods of the one or more first and second likelihoods. The one or more field programmable gate arrays also may be further configured to transfer the one or more candidate alignment locations having the currently greater likelihoods for mapping of the short read using a next, third partition of the plurality of reference genome index partitions.

In a representative embodiment, the one or more field programmable gate arrays are further configured to hash the selected seed and use the hashed seed to access the reference genome index. Also in a representative embodiment, the one or more field programmable gate arrays are further configured to generate a forward sequence and a reverse complement sequence for the selected seed; to determine which of the forward sequence or the reverse complement sequence is lexicographically smaller; to hash the lexicographically smaller sequence to produce a hash result; and to use the hash result as the hashed seed to access the reference genome index.

As mentioned above, in a representative embodiment, the reference genome index comprises a pointer table and a candidate alignment location table. For such an embodiment, the one or more field programmable gate arrays are further configured to use the first predetermined number of the most significant bits of the selected hashed seed to access the pointer table to obtain a corresponding pointer; and to use the corresponding pointer and the second predetermined number of the least significant bits of the selected hashed seed to determine the candidate alignment location.

In a representative embodiment, a system may further comprise a host computing system to create the reference genome index. For such an embodiment, the host computing system further is to determine all <seed, location> tuples in the reference genome sequence to form a plurality of <seed, location> tuples; to sort and eliminate redundant tuples from the plurality of <seed, location> tuples; for each seed, to generate a forward sequence and a reverse complement sequence and determine which of the forward sequence or the reverse complement sequence is lexicographically smaller; for each seed, to hash the lexicographically smaller sequence to produce a hash result; and for each seed, to use the hash result as the hashed seed for the reference genome index.

Also for such an embodiment, the host computing system further is to create a pointer table, each entry of the pointer table comprising a first predetermined number of the most significant bits of the selected hashed seed and a corresponding pointer; and create a candidate alignment location table, each entry of the candidate alignment location table comprising a second predetermined number of the least significant bits of the selected hashed seed and a corresponding candidate alignment location.

Also in a representative embodiment, the one or more field programmable gate arrays are further configured to filter the plurality of candidate alignment locations to eliminate any redundant candidate alignment locations.

In a representative embodiment, the one or more field programmable gate arrays are further configured to perform a Smith-Waterman string matching of the short read with the reference genome sequence to determine the likelihood of the short read matching the reference genome sequence. For such an embodiment, the one or more field programmable gate arrays are further configured to perform a plurality of Smith-Waterman string matching operations in parallel.

In a representative embodiment the one or more field programmable gate arrays are further configured to determine the vicinity of the candidate alignment location as a sequence beginning at the start of the candidate alignment location minus a predetermined offset and extending through the end of the candidate alignment location plus a length of the selected short read and the predetermined offset.

Also in a representative embodiment, the one or more field programmable gate arrays are further configured to perform the selections, extraction, and determinations in parallel.

Also in a representative embodiment, the reference genome sequence is divided into a plurality of reference blocks, each reference block having a size corresponding to a single read from the one or more memory circuits.

A representative system for acceleration of short read mapping to a reference genome sequence for genomic analysis may comprise: one or more memory circuits storing a plurality of short reads, a reference genome sequence, and a reference genome index, each short read comprising a sequence of a plurality of genetic bases, the reference genome index comprising a pointer table and a candidate alignment location table; and one or more field programmable gate arrays coupled to the one or more memory circuits, the one or more field programmable gate arrays configured to select a short read from the plurality of short reads; to extract a plurality of seeds from the short read, each seed comprising a genetic subsequence of the short read; for each seed of the plurality of seeds, to generate a forward sequence and a reverse complement sequence for the selected seed and determine which of the forward sequence or the reverse complement sequence is lexicographically smaller; to hash the lexicographically smaller sequence to produce a hash result; to use the hash result to access the reference genome index to determine a candidate alignment location in the reference genome sequence to form a plurality of candidate alignment locations; for each candidate alignment location of the plurality of candidate alignment locations, to perform string matching to determine a likelihood of the short read matching the reference genome sequence in the vicinity of the candidate alignment location; and to select a candidate alignment location, of the plurality of candidate alignment locations, having the currently greatest likelihood of the short read matching the reference genome sequence.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which:

FIG. 18 illustrates an exemplary or representative fully aligned read and the backtracking process.

DETAILED DESCRIPTION OF REPRESENTATIVE EMBODIMENTS

Figure 1:
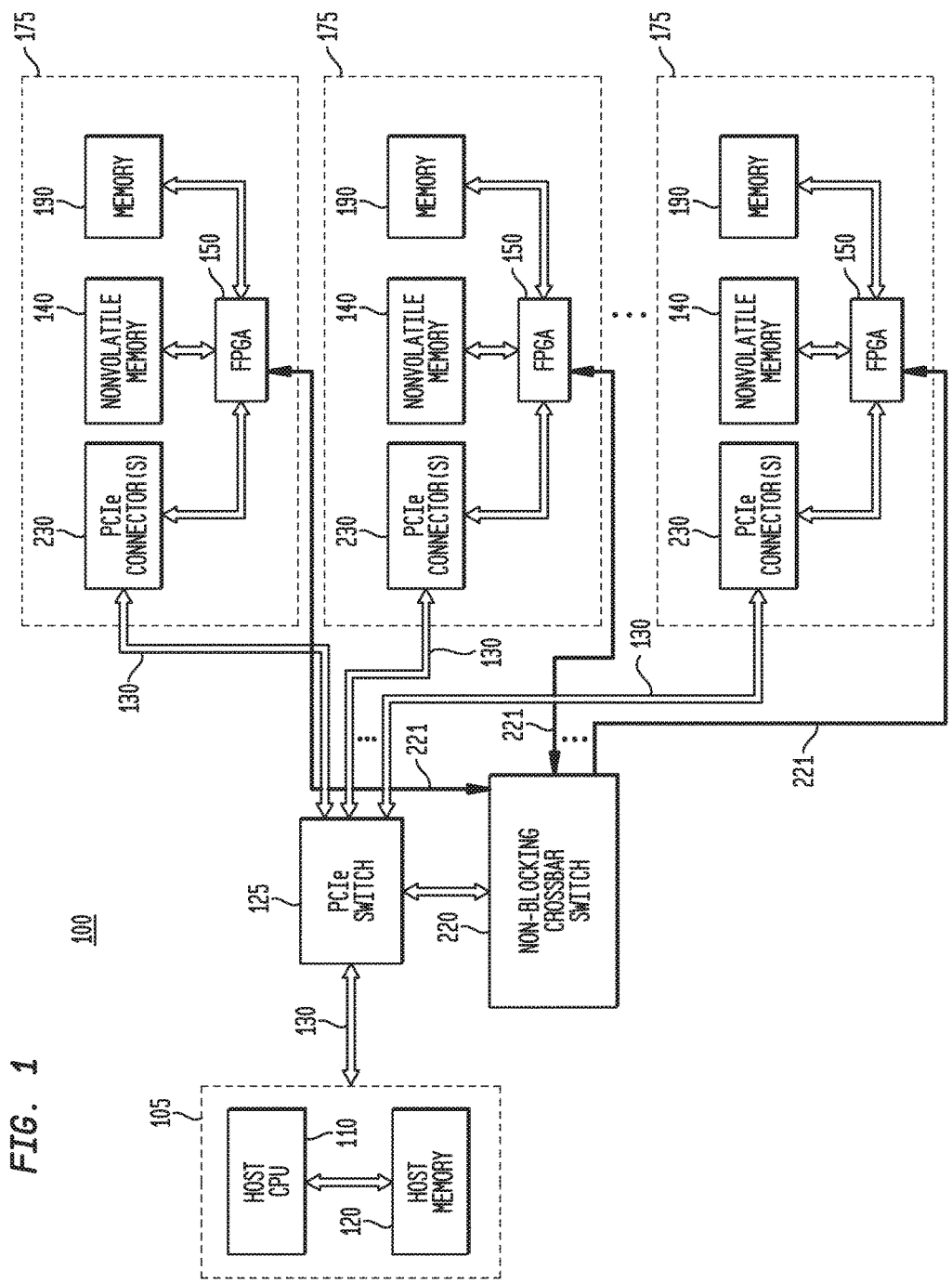
FIG. 1 is a block diagram illustrating an exemplary or representative first system embodiment.

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

Figure 2:
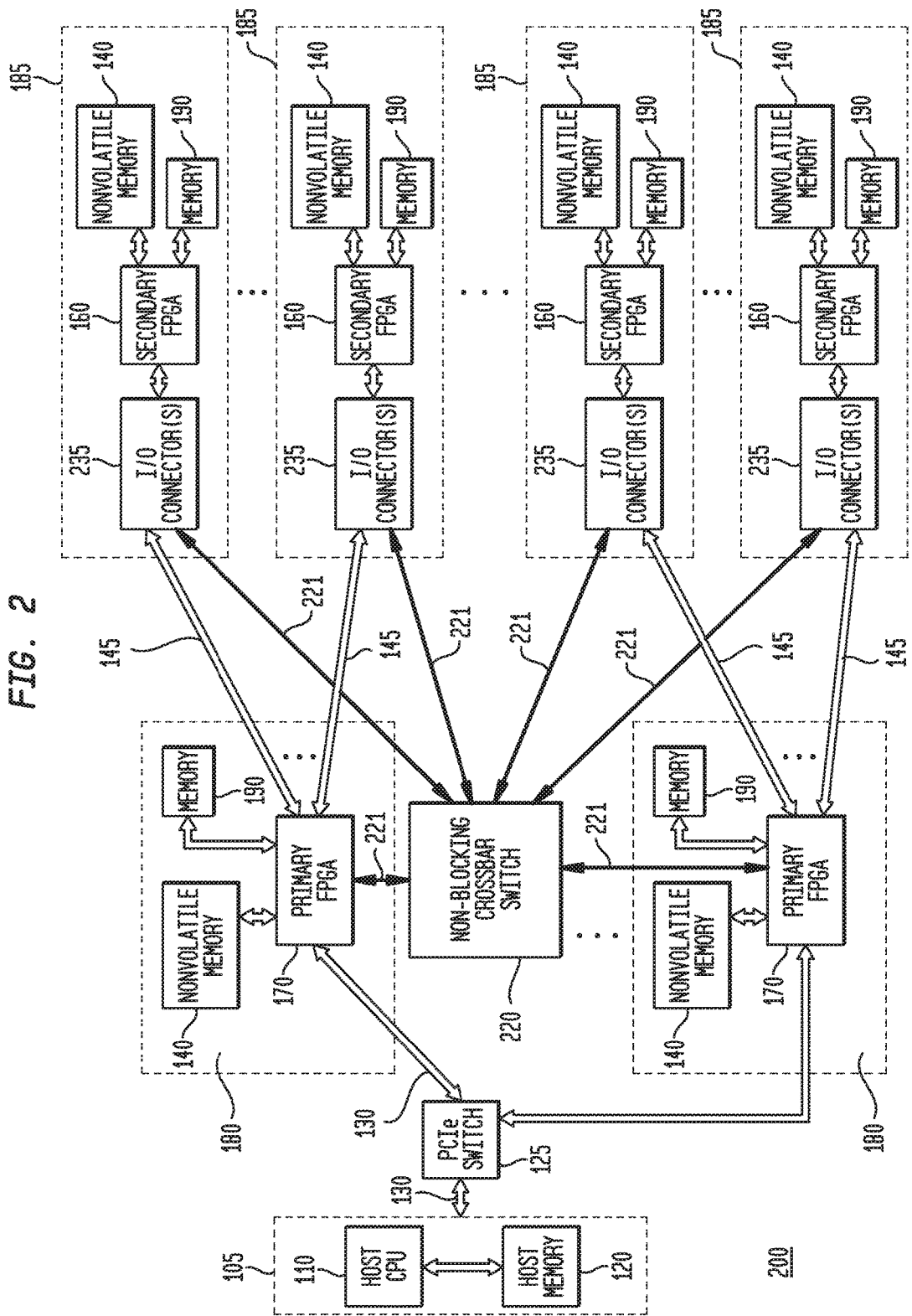
FIG. 2 is a block diagram illustrating an exemplary or representative second system embodiment.
Figure 3:
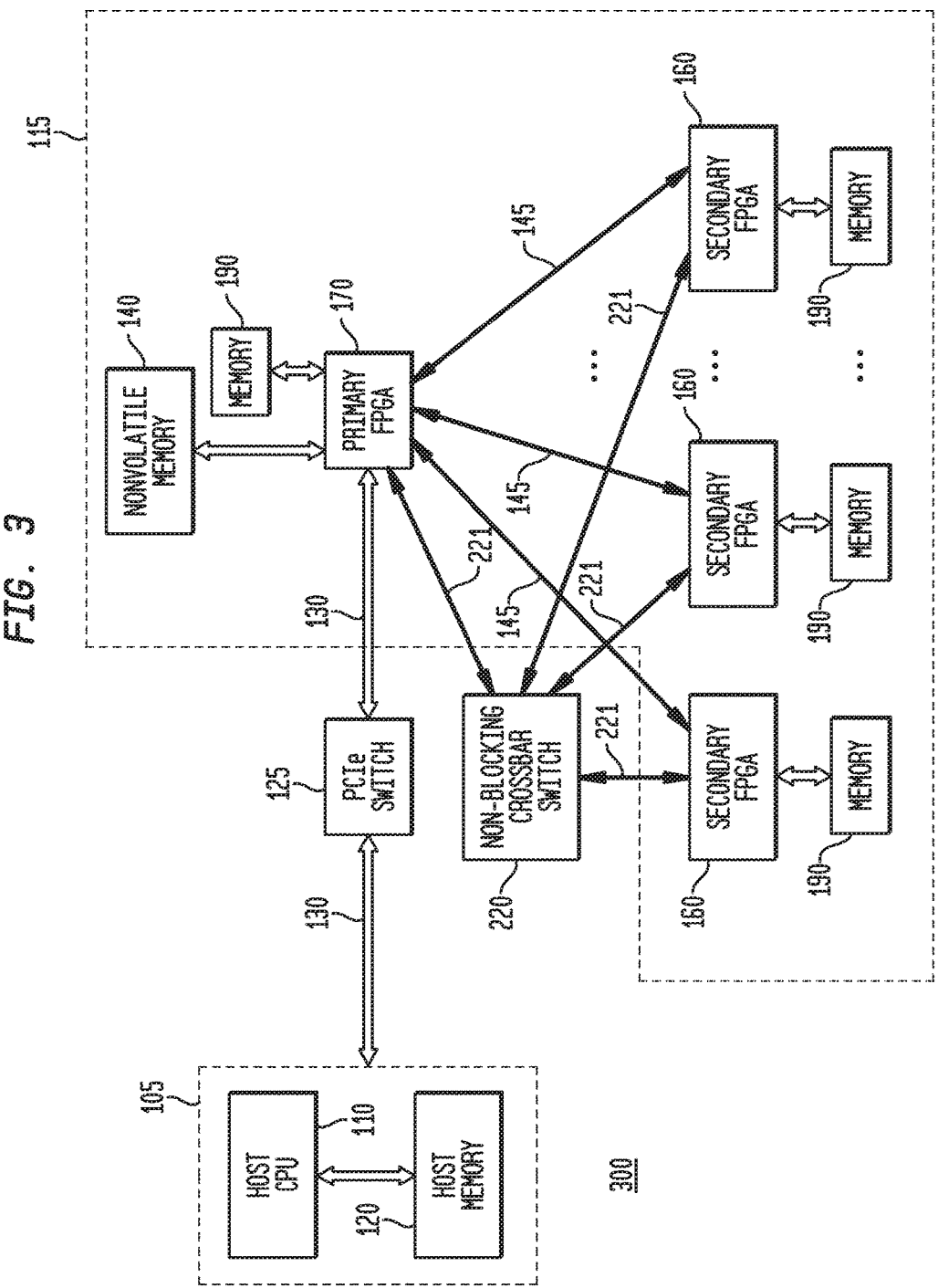
FIG. 3 is a block diagram illustrating an exemplary or representative third system embodiment.
Figure 4:
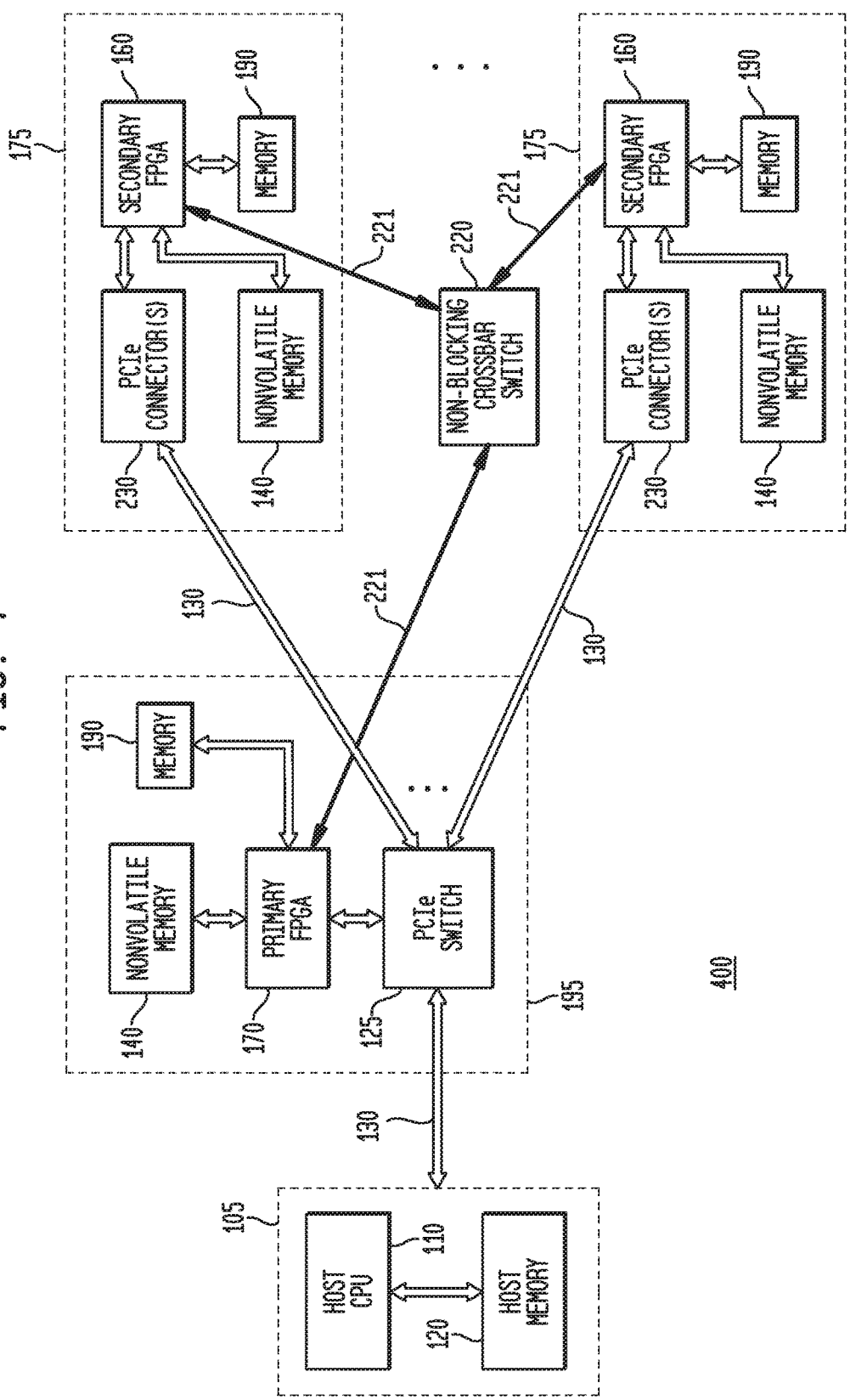
FIG. 4 is a block diagram illustrating an exemplary or representative fourth system embodiment.

FIG. 1 is a block diagram illustrating an exemplary or representative first system 100 embodiment. FIG. 2 is a block diagram illustrating an exemplary or representative second system 200 embodiment. FIG. 3 is a block diagram illustrating an exemplary or representative third system 300 embodiment and first apparatus embodiment. FIG. 4 is a block diagram illustrating an exemplary or representative fourth system 400 embodiment.

As illustrated in FIGS. 1-4, the systems 100, 200, 300, 400 include one or more host computing systems 105, such as a computer or workstation, having one or more central processing units (CPUs) 110, which may be any type of processor, and host memory 120, which may be any type of memory, such as a hard drive or a solid state drive, and which may be located with or separate from the host CPU 110, all for example and without limitation, and as discussed in greater detail below. The memory 120 typically stores data to be utilized in or was generated by a selected application and also generally a configuration bit file or image for a selected application. Not separately illustrated, any of the host computing systems 105 may include a plurality of different types of processors, such as graphics processors, multi-core processors, etc., also as discussed in greater detail below. The various systems 100, 200, 300, 400 differ from one another in terms of the arrangements of circuit components, types of components, and types of communication between and among the various components, as described in greater detail below.

The one or more host computing systems 105 are typically coupled through one or more communication channels or lines, illustrated as PCI express (Peripheral Component Interconnect Express or "PCIe") lines 130, either directly or through a PCIe switch 125, to one or more configurable logic elements such as one or more FPGAs 150 (such as a Spartan 6 FPGA or a Kintex-7 FPGA, both available from Xilinx, Inc. of San Jose, Calif., US, or a Stratix 10 or Cyclone V FPGA available from Altera Corp. of San Jose, Calif., US, for example and without limitation), each of which in turn is coupled to a nonvolatile memory 140, such as a FLASH memory (such as for storing configuration bit images), and to a plurality of random access memories 190, such as a plurality of DDR3 (SODIMM) memory integrated circuits. In a first embodiment as illustrated, each FPGA 150 and corresponding memories 140, 190 directly coupled to that FPGA 150 are collocated on a corresponding computing module (or circuit board) 175 as a module or board in a rack mounted system having many such computing modules 175, such as those available from Pico Computing of Seattle, Wash. US. As illustrated, each computing module 175 includes as an option a PCIe input and output (I/O) connector 230 to provide the PCIe 130 connections, such as for a rack mounted system. The PCIe switch 125 may be located or positioned anywhere in a system 100, 200, 300, 400, such as on a separate computing module (such as a backplane circuit board), or on any of the computing modules 175, 180, 185, 195, 115 for example and without limitation. In addition, other types of communication lines or channels may be utilized to couple the one or more host computing systems 105 to the FPGAs 150, such as an Ethernet line, which in turn may be coupled to other intervening rack-mounted components to provide communication to and from one or more FPGAs 150 (160, 170) and other modules.

In addition to communication over PCIe communication lines 130 via PCIe switch 125 (e.g., available from PLX Technology, Inc. of Sunnyvale, Calif., US), another significant feature of the systems 100, 200, 300, 400 is the use of one or more non-blocking crossbar switches 220. The non-blocking crossbar switch 220 provides for pairwise and concurrent communication (lines 221) between and among the FPGAs 150, 160, 170, without communication between any given pair of FPGAs 150, 160, 170 blocking any other communication between another pair of FPGAs 150, 160, 170. In exemplary embodiment, one or more non-blocking crossbar switches 220 are provided to have sufficient capacity to enable direct FPGA to FPGA communication between and among all of the FPGAs 150, 160, 170 in a selected portion of the system 100, 200. In a representative embodiment, one or more non-blocking crossbar switches 220 are implemented using one or more FPGAs 150, 160, 170 which have been configured accordingly.

Referring to FIG. 2, the system 200 differs insofar as the various FPGAs are hierarchically organized into one or more primary (or central) configurable logic elements such as primary FPGAs 170 (also such as a Spartan 6 FPGA or any of the other FPGAs mentioned above, for example and without limitation) and a plurality of secondary (or remote) configurable logic elements such as one or more secondary FPGAs 160. The one or more host computing systems 105 are typically coupled through one or more communication channels or lines, illustrated as PCI express (Peripheral Component Interconnect Express or "PCIe") lines 130, either directly or through a PCIe switch 125, to primary FPGAs 170, each of which in turn is coupled to a plurality of secondary FPGAs 160, also through one or more corresponding communication channels, illustrated as a plurality of JTAG lines 145 (Joint Test Action Group ("JTAG") is the common name for the IEEE 1149.1 Standard Test Access Port and Boundary-Scan Architecture). In this embodiment, (illustrated in FIG. 2), each of the secondary FPGAs 160 is provided on a separate computing module 185 which is couplable to the computing module 180 having the primary FPGA 170.

The PCIe switch 125 may be positioned anywhere in a system 100, 200, 300, 400, such as on a separate computing module, for example and without limitation, or on one or more of the computing modules 180 having the primary FPGA 170, as illustrated in FIG. 4 for computing module 195. In an exemplary embodiment, due to a significantly large fan out of the PCIe lines 130 to other modules and cards in the various systems 100, 200, 300, 400, the PCIe switch 125 is typically located on the backplane of a rack-mounted system (available from Pico Computing, Inc. of Seattle, Wash. US). A PCIe switch 125 may also be collocated on various computing modules (e.g., 195), to which many other modules (e.g., 175) connect (e.g., through PCIe connector(s) 230). In addition, other types of communication lines or channels may be utilized to couple the one or more host computing systems 105 to the primary FPGAs 170 and or secondary FPGAs 160, such as an Ethernet line, which in turn may be coupled to other intervening rack-mounted components to provide communication to and from one or more primary FPGAs 170 and other modules.

In this system 200 embodiment, the primary and secondary FPGAs 170 and 160 are located on separate computing modules 180 and 185, also in a rack mounted system having many such computing modules 180 and 185, also such as those available from Pico Computing of Seattle, Wash. US. The computing modules 180 and 185 may be coupled to each other via any type of communication lines, including PCIe and/or JTAG. For example, in an exemplary embodiment, each of the secondary FPGAs 160 is located on a modular computing module (or circuit board) 185 which have corresponding I/O connectors 235 to plug into a region or slot of the primary FPGA 170 computing module 180, up to the capacity of the primary FPGA 170 computing module 180, such as one to six modular computing modules 185 having secondary FPGAs 160. For purposes of the present disclosure, systems 100, 200, 300, 400 function similarly, and any and all of these system configurations are within the scope of the disclosure.

Not separately illustrated in FIGS. 1-4, each of the various computing modules 175, 180, 185, 195, 115 typically include many additional components, such as power supplies, additional memory, additional input and output circuits and connectors, switching components, etc.

The various systems 100, 200, 300, 400 may also be combined into a plurality of system configurations, such as mixing the different types of FPGAs 150, 160, 170 and computing modules 175, 180, 185, 195, 115 into the same system, including within the same rack-mounted system.

Additional representative system 300, 400 configurations or arrangements are illustrated in FIGS. 3 and 4. In the system 300 embodiment, the primary and secondary FPGAs 150 and 160 are collocated on a dedicated computing module 115 as a module in a rack mounted system having many such computing modules 115, such as those available from Pico Computing of Seattle, Wash. US. In the system 400 embodiment, (illustrated in FIG. 4), each of the secondary FPGAs 160 is provided on a separate computing module 175 which is couplable to the computing module 195 having the primary FPGA 170. PCIe switches 125 are also illustrated as collocated on computing module 195 for communication with secondary FPGAs 160 over PCIe communication lines 130, although this is not required and such a PCIe switch 125 may be positioned elsewhere in a system 100, 200, 300, 400, such as on a separate computing module, for example and without limitation.

As a consequence, for purposes of the present disclosure, a system 100, 200, 300, 400 comprises one or more host computing systems 105, couplable through one or more communication lines (such as PCIe communication lines (130), directly or through a PCIe switch 125), to one or more FPGAs 150 and/or primary FPGAs 170. In turn, each primary FPGA 170 is coupled through one or more communication lines, such as JTAG lines 145 or PCIe communication lines 130, to one or more secondary FPGAs 160. Depending upon the selected embodiment, each FPGA 150, 160, 170 is coupled to a non-blocking crossbar switch 220 for pairwise communication with any other FPGA 150, 160, 170. In addition, each FPGA 150, 160, 170 is typically coupled to one or more nonvolatile memories 140 and one or more random access memories 190, which may be any type of random access memory.

Significant features are enabled in the system 100, 200, 300, 400 as an option, namely, the highly limited involvement of the host CPU 110 in configuring any and all of the FPGAs 150, 160, 170, which frees the host computing system 105 to be engaged in other tasks. In addition, the configuration of the FPGAs 150, 160, 170 may be performed in a massively parallel process, allowing significant time savings. Moreover, because the full configurations of the FPGAs 150, 160, 170 are not required to be stored in nonvolatile memory 140 (such as FLASH), with corresponding read/write cycles which are comparatively slow, configuration of the FPGAs 150, 160, 170 may proceed at a significantly more rapid rate, including providing new or updated configurations. The various FPGAs 150, 160, 170 may also be configured as known in the art, such as by loading a complete configuration from nonvolatile memory 140.

Another significant feature of the systems 100, 200, 300, 400 is that only basic (or base) resources for the FPGAs 150 or primary FPGAs 170 are stored in the nonvolatile memory 140 (coupled to a FPGA 150 or a primary FPGA 170), such as a configuration for communication over the PCIe lines 130 (and possibly JTAG lines 145, such as for secondary FPGAs 160), and potentially also a configuration for one or more DMA engines (depending upon the selected FPGA, the FPGA may be available with incorporated DMA engines). As a result, upon system 100, 200, 300, 400 startup, the only configurations required to be loaded into the FPGA 150 or primary FPGA 170 is limited or minimal, namely, communication (e.g., PCIe and possibly JTAG) functionality and or DMA functionality. In a representative embodiment, upon system 100, 200, 300, 400 startup, the only configuration required to be loaded into the FPGA 150 or a primary FPGA 170 is a communication configuration for PCIe functionality. As a consequence, this base PCIe configuration may be loaded quite rapidly from the nonvolatile memory 140. Stated another way, except for loading of the base communication configuration for PCIe functionality, use of the nonvolatile memory 140 for FPGA configuration is bypassed entirely, both for loading of an initial configuration or an updated configuration.

Instead of a host CPU 110 "bit banging" or transferring a very large configuration bit image to each FPGA 150 or primary FPGA 170, configuration of the system 100, 200, 300, 400 occurs rapidly and in parallel when implemented in representative embodiments. Configuration of the FPGAs 150 or primary FPGAs 170 and secondary FPGAs 160 begins with the host CPU 110 merely transmitting a message or command to one or more FPGAs 150 or primary FPGAs 170 with a memory address or location in the host memory 120 (and typically also a file size) of the configuration bit image (or file) which has been stored in the host memory 120, i.e., the host CPU 110 sets the DMA registers of the FPGA 150 or primary FPGA 170 with the memory address and file size for the selected configuration bit image (or file) in the host memory 120. Such a "load FPGA" command is repeated for each of the FPGAs 150 or primary FPGAs 170 (and possibly each secondary FPGA 160, depending upon the selected embodiment), i.e., continuing until the host CPU 110 does not find any more FPGAs 150 or primary FPGAs 170 (and/or secondary FPGAs 160) in the system 100, 200, 300, 400 and an error message may be returned. Typically, the host CPU 110 transmits one such message or command to each FPGA 150 or primary FPGA 170 that will be handling a thread of a parallel, multi-threaded computation. In the representative embodiments, the host CPU 110 is then literally done with the configuration process, and is typically notified with an interrupt signal from a FPGA 150 or primary FPGA 170 once configuration is complete. Stated another way, from the perspective of the host computing system 105, following transmission of generally a single message or command having a designation of a memory address (and possibly a file size), the configuration process is complete. This is a huge advance over prior art methods of FPGA configuration in supercomputing systems.

Using a DMA engine, along with communication lines such PCIe lines 130 which support communication of large bit streams, each FPGA 150 or primary FPGA 170 then accesses the host memory 120 and obtains the configuration bit image (or file) (which configuration also generally is loaded into the FPGA 150 or primary FPGA 170). By using the DMA engine, much larger files may be transferred quite rapidly, particularly compared to any packet- or word-based transmission (which would otherwise have to be assembled by the host CPU 110, a comparatively slow and labor-intensive task). This is generally performed in parallel (or serially, depending upon the capability of the host memory 120) for all of the FPGAs 150 or primary FPGAs 170. In turn, each primary FPGA 170 then transmits (typically over JTAG lines 145 or PCIe communication lines 130) the configuration bit image (or file) to each of the secondary FPGAs 160, also typically in parallel. Alternatively, each primary FPGA 150 may re-transmit (typically over JTAG lines 145 or PCIe communication lines 130) the information of the load FPGA message or command to each of the secondary FPGAs 160, namely the memory address in the host memory 120 and the file size, and each secondary FPGA 160 may read or otherwise obtain the configuration bit image, also using DMA engines, for example and without limitation. As another alternative, the host computing system 105 may transmit the load FPGA message or command to each of the FPGAs 150 or primary FPGAs 170 and secondary FPGAs 160, which then obtain the configuration bit image, also using DMA engines as described above. All such variations are within the scope of the disclosure.

By using communication lines such as PCIe lines 130 and JTAG lines 145 with the design of the system 100, 200, 300, 400, the configuration bit image is loaded quite rapidly into not only into each of the FPGAs 150 and primary FPGAs 170 but also into each of the secondary FPGAs 160. This allows not only for an entire computing module 175 (or computing modules 180, 185, 195) to be reloaded in seconds, rather than hours, but the entire system 100, 200, 300, 400 may be configured and reconfigured in seconds, also rather than hours. As a result, read and write operations to local memory (e.g., nonvolatile memory 140) largely may be bypassed almost completely in the configuration process, resulting in a huge time savings. In selected embodiments, if desired but certainly not required, the configuration bit image (or file) may also be stored locally, such as in nonvolatile memory 140 (and/or nonvolatile memory 190 (e.g., FLASH) associated with computing modules 175, 180, 185, 195, 115).

As a result of this ultrafast loading of configurations, another significant advantage of the system 100, 200, 300, 400 is the corresponding capability, using the same process, for ultrafast reconfiguration of the entire system 100, 200, 300, 400. This is particularly helpful for the design, testing and optimization of system 100, 200, 300, 400 configurations for any given application, including various computationally intensive applications such as bioinformatics applications (e.g., gene sequencing).

Figure 5:
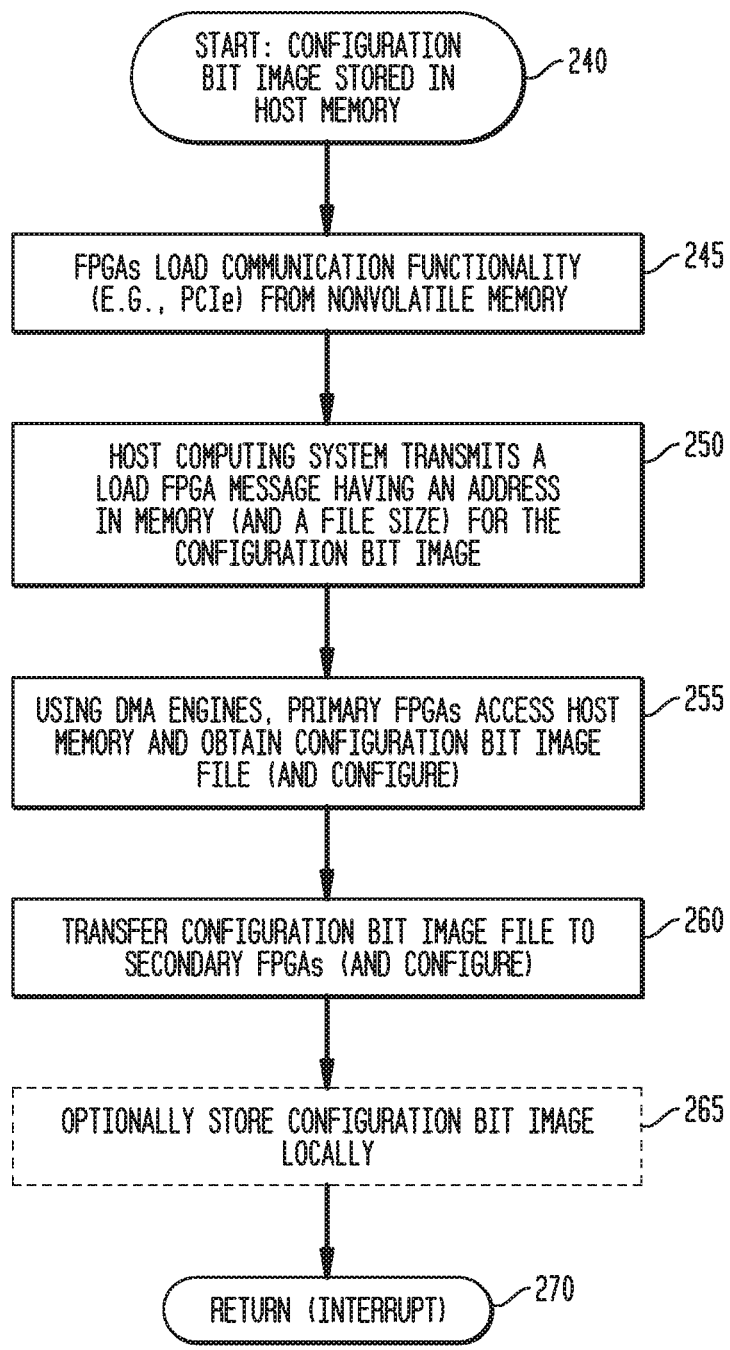
FIG. 5 is a flow diagram illustrating an exemplary or representative configuration method embodiment.

FIG. 5 is a flow diagram illustrating an exemplary or representative method embodiment for system configuration and reconfiguration, and provides a useful summary of this process. Beginning with start step 240 and one or more FPGA 150, 160, 170 configurations (as configuration bit images) having been stored in a host memory 120, the system 100, 200, 300, 400 powers on or otherwise starts up, and the FPGAs 150, 160, 170 load the base communication functionality such as a PCIe configuration image (and possibly DMA functionality) from nonvolatile memory 140, step 245. The host CPU 110 (or more generally, host computing system 105) then generates and transmits a "load FPGA" command or message to one or more FPGAs 150 or primary FPGAs 170 (and/or secondary FPGAs 160), step 250, in which the load FPGA command or message includes a starting memory address (in host memory 120) and a file size designation for the selected configuration bit image which is to be utilized. Using the DMA engines, and depending upon the selected variation (of any of the variations described above), the one or more FPGAs 150 or primary FPGAs 170 (and/or secondary FPGAs 160) obtain the configuration bit image from the host memory 120, step 255, and use it to configure. Also depending upon the selected embodiment, the one or more FPGAs 150 or primary FPGAs 170 may also transfer the configuration bit image to each of the secondary FPGAs 160, step 260, such as over JTAG lines 145 and bypassing nonvolatile memory 140, 190, which the secondary FPGAs 160 also use to configure. Also depending upon the selected embodiment, the configuration bit image may be stored locally, step 265, as a possible option as mentioned above. Having loaded the configuration bit image into the FPGAs 150, 160, 170, the method may end, return step 270, such as by generating an interrupt signal back to the host computing system 105.

The systems 100, 200, 300, 400 enable one of the significant features of the present disclosure, namely, the highly limited involvement of the host CPU 110 in data transfers between the host computing system 105 and any of the FPGAs 150, 160, 170, and their associated memories 190, and additionally, the highly limited involvement of the host CPU 110 in data transfers between and among any of the FPGAs 150, 160, 170, and their associated memories 190, all of which frees the host computing system 105 to be engaged in other tasks, and further is a significant departure from prior art systems. Once data transfer directions or routes have been established for a given or selected application within the systems 100, 200, 300, 400, moreover, these data communication paths are persistent for the duration of the application, continuing without any further involvement by the host computing system 105, which is also a sharp contrast with prior art systems.

Instead of a host CPU 110 "bit banging" or transferring a data file, including a very large data file, to each FPGA 150, 160, 170 or its associated memories 190, data transfers within the system 100, 200, 300, 400 occur rapidly and in parallel, and following setup of the DMA registers in the various FPGAs 150, 160, 170, largely without involvement of the host computing system 105. The data transfer paths are established by the host CPU 110 merely transmitting a message or command to one or more FPGAs 150, 160, 170 to set the base DMA registers within the FPGA 150, 160, 170 with a memory 190 address (or address or location in the host memory 120, as the case may be), a file size of the data file, and a stream number, i.e., the host CPU 110 (or another FPGA 150, 160, 170 configured for this task) sets the DMA registers of the FPGA 150, 160, 170 with the memory address and file size for the selected data file in the host memory 120 or in one of the memories 190, and also assigns a stream number, including a tie (or tied) stream number if applicable. Once this is established, the system 100, 200, 300, 400 is initialized for data transfer, and these assignments persist for the duration of the application, and do not need to be re-established for subsequent data transfers.

The host CPU 110 (or an FPGA 150, 160, 170 configured for this task) has therefore established the various data transfer paths between and among the host computing system 105 and the FPGAs 150, 160, 170 for the selected application. As data is then transferred throughout the system 100, 200, 300, 400, header information for any data transfer includes not only a system address (e.g., PCIe address) for the FPGA 150, 160, 170 and/or its associated memories 190, but also includes the "stream" designations (or information) and "tie (or tied) stream" designations (or information), and is particularly useful for multi-threaded or other parallel computation tasks. The header (e.g., a PCIe data packet header) for any selected data transfer path includes: (1) bits for an FPGA 150, 160, 170 and/or memory 190 address and file size; (2) additional bits for an assignment a stream number to the data transfer (which stream number can be utilized repeatedly for additional data to be transferred subsequently for ongoing computations); and (3) additional bits for any "tie stream" designations, if any are utilized or needed. In addition, as each FPGA 150, 160, 170 may be coupled to a plurality of memories 190, each memory address typically also includes a designation of which memory 190 associated with the designated FPGA 150, 160, 170.

Figure 6:
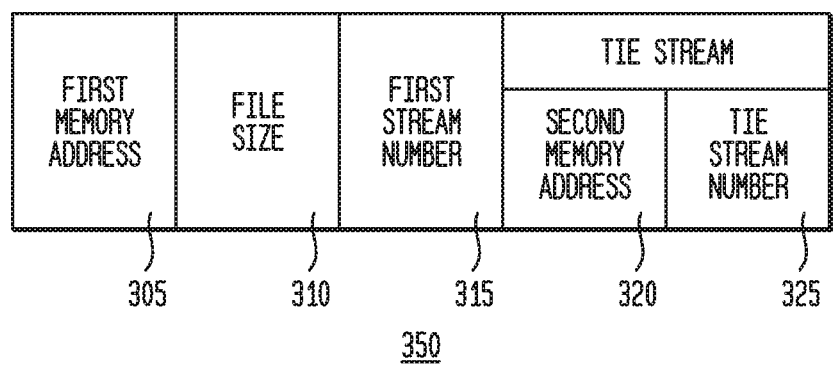
FIG. 6 is a block diagram illustrating exemplary or representative fields for a (stream) packet header.

FIG. 6 is a block diagram illustrating exemplary or representative fields for a (stream) packet header 350, comprising a plurality of bits designating a first memory address (field 305) (typically a memory 190 address), a plurality of bits designating a file size (field 310), a plurality of bits designating a (first) stream number (field 315), and as may be necessary or desirable, two additional and optional tie stream fields, namely, a plurality of bits designating the (second) memory 190 address for the tied stream (field 320) and a plurality of bits designating a tie (or tied) stream number (field 325).

Any application may then merely write to the selected stream number or read from the selected stream number for the selected memory 190 address (or FPGA 150, 160, 170 address), without any involvement by the host computing system 105, for as long as the application is running on the system 100, 200. In addition, for data transfer throughout the systems 100, 200, data transfer in one stream may be tied to a data transfer of another stream, allowing two separate processes to occur without involvement of the host computing system 105. The first "tie stream" process allows the "daisy chaining" of data transfers, so a data transfer to a first stream number for a selected memory 190 (or FPGA 150, 160, 170 process) on a first computing module 175, 180, 185, 195, 115 may be tied or chained to a subsequent transfer of the same data to another, second stream number for a selected memory 190 (or FPGA 150, 160, 170 process) on a second computing module 175, 180, 185, 195, 115, e.g., data transferred from the host computing system 105 or from a first memory 190 on a first computing module 175, 180, 185, 195, 115 (e.g., card "A") (stream "1") to a second memory 190 on a second computing module 175, 180, 185, 195, 115 (e.g., card "B") will also be further transmitted from the second computing module 175, 180, 185, 195, 115 (e.g., card "B") as a stream "2" to a third memory 190 on a third computing module 175, 180, 185, 195, 115 (e.g., card "C"), thereby tying streams 1 and 2, not only for the current data transfer, but for the entire duration of the application (until changed by the host computing system 105).

The second "tie stream" process allows the chaining or sequencing of data transfers between and among any of the FPGAs 150, 160, 170 without any involvement of the host computing system 105 after the initial setup of the DMA registers in the FPGAs 150, 160, 170. As a result, a data result output from a first stream number for a selected memory 190 (or FPGA 150, 160, 170 process) on a first computing module 175, 180, 185, 195, 115 may be tied or chained to be input data for another, second stream number for a selected memory 190 (or FPGA 150, 160, 170 process) on a second computing module 175, 180, 185, 195, 115, e.g., stream "3" data transferred from the a first memory 190 on a first computing module 175, 180, 185, 195, 115 (e.g., card "A") will transferred as a stream "4" to a second memory 190 on a second computing module 175, 180, 185, 195, 115 (e.g., card "B"), thereby tying streams 3 and 4, not only for the current data transfer, but for the entire duration of the application (also until changed by the host computing system 105).

Any of these various data transfers may occur through any of the various communication channels of the systems 100, 200, 300, 400, in addition to transmission over the PCIe network (PCIe switch 125 with PCIe communication lines 130), including through the non-blocking crossbar switch 220 and over the JTAG lines 145, depending upon the selected system 100, 200, 300, 400 configuration. All of these various mechanisms provide for several types of direct FPGA-to-FPGA communication, without any ongoing involvement by host computing system 105 once the DMA registers have been established. Stated another way, in the representative embodiments, the host CPU 110 is then literally done with the data transfer process, and from the perspective of the host computing system 105, following transmission of the DMA setup messages having a designation of a memory 190 address, a file size, and a stream number, the data transfer configuration process is complete. This is a huge advance over prior art methods of data transfer in supercomputing systems utilizing FPGAs.

Using a DMA engine, along with communication lines such PCIe lines 130 which support communication of large bit streams, each FPGA 150, 160, 170 then accesses the host memory 120 or a memory 190 and obtains the data file for a read operation, or performs a corresponding write operation, all using the established address and stream number. By using the DMA engine, much larger files may be transferred quite rapidly, particularly compared to any packet- or word-based transmission. This is generally performed in parallel (or serially, depending upon the application) for all of the FPGAs 150, 160, 170.

By using communication lines such as PCIe lines 130 and JTAG lines 145 with the design of the system 100, 200, 300, 400, data transfer occurs quite rapidly, not only into each of the FPGAs 150 or primary FPGAs 170 but also into each of the secondary FPGAs 160, and their associated memories 190. As a result, resources, including memory 190, may be shared across the entire system 100, 200, 300, 400, with any FPGA 150, 160, 170 being able to access any resource anywhere in the system 100, 200, 300, 400, include any of the memories 190 on any of the computing modules or cards (modules) 175, 180, 185, 195, 115.

Figure 7:
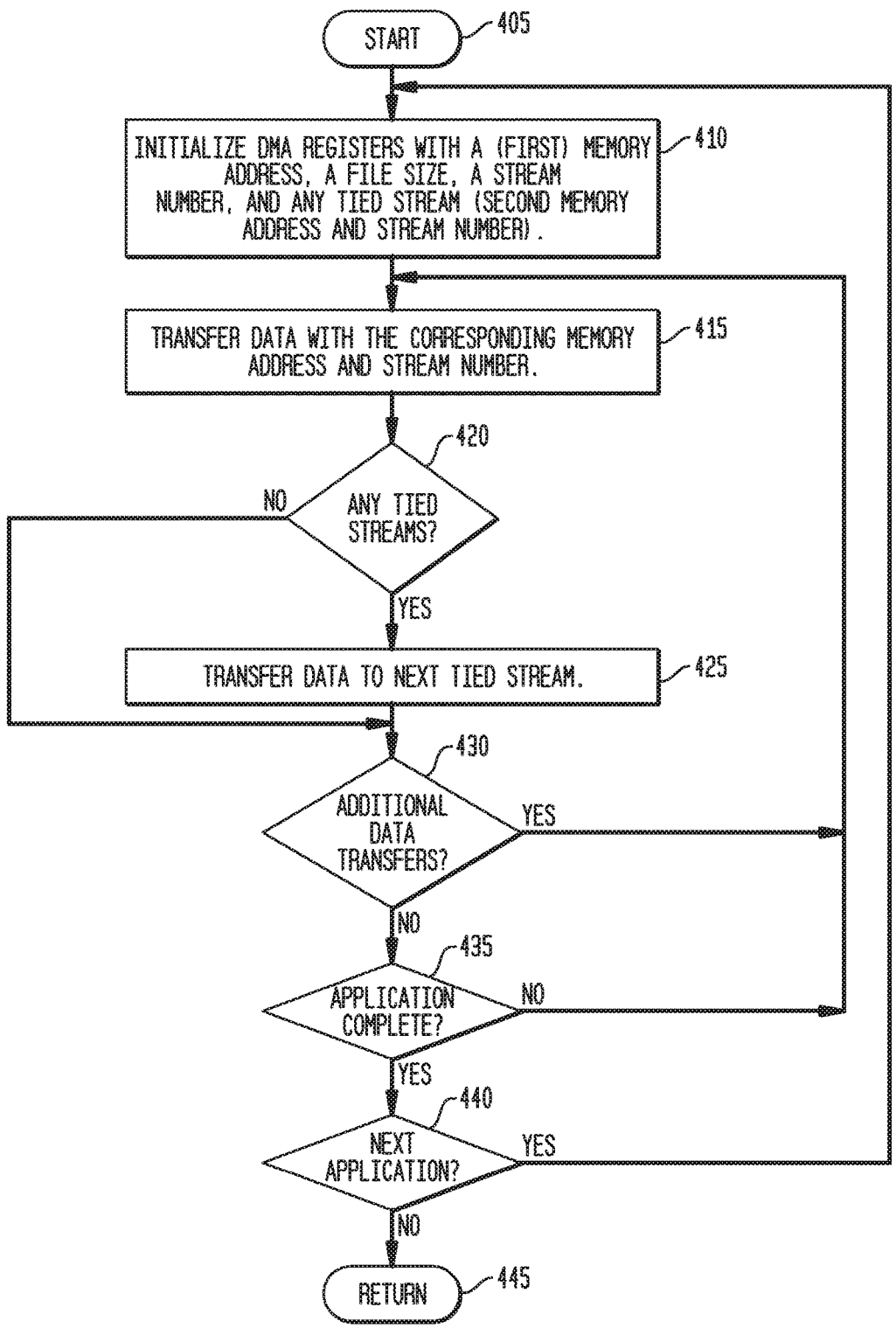
FIG. 7 is a flow diagram illustrating an exemplary or representative communication method embodiment.

FIG. 7 is a flow diagram illustrating an exemplary or representative method embodiment for data transfer within a system 100, 200, 300, 400 and provides a useful summary. Beginning with start step 405, one or more DMA registers associated with any of the FPGAs 150, 160, 170 and their associated memories 190 are setup, step 410, with a memory (120, 190) address, a file size, a stream number, and any tie (or tied) stream number. Using the DMA engines for read and write operations, or using other available configurations within FPGAs 150, 160, 170, data is transferred between and among the FPGAs 150, 160, 170 using the designated addresses and stream numbers, step 415. When there are any tied streams, step 420, then the data is transferred to the next tied stream, step 425, as the case may be. When there are additional data transfers, step 430, the method returns to step 415, and the process iterates. Otherwise, the method determines whether the application is complete, step 435, and if not, returns to step 415 and iterates as well. When the application is complete in step 435, and there is another application to be run, step 440, the method returns to step 410 to set up the DMA registers for the next application, and iterates. When there are no more applications to be run, the method may end, return step 445.

The systems 100, 200, 300, 400 as described above may be utilized quite advantageously to accurately and rapidly solve the short read mapping problem referred to above, and determine the location in the reference genome to which each short read maps best. Alternatively, the systems 100, 200, 300, 400 may also be configured to provide several (e.g., the top one, two or three) alignment locations for a short read. The increased performance can be used to speed up genome sequencing, or to allow the use of more sensitive short read mapping algorithms, which are able to map a greater percentage of the reads to the reference genome. The process and configuration used for genetic mapping by the systems 100, 200, 300, 400 may also be applied advantageously to other bioinformatics problems, such as in proteomics, for example and without limitation.

Figure 8:
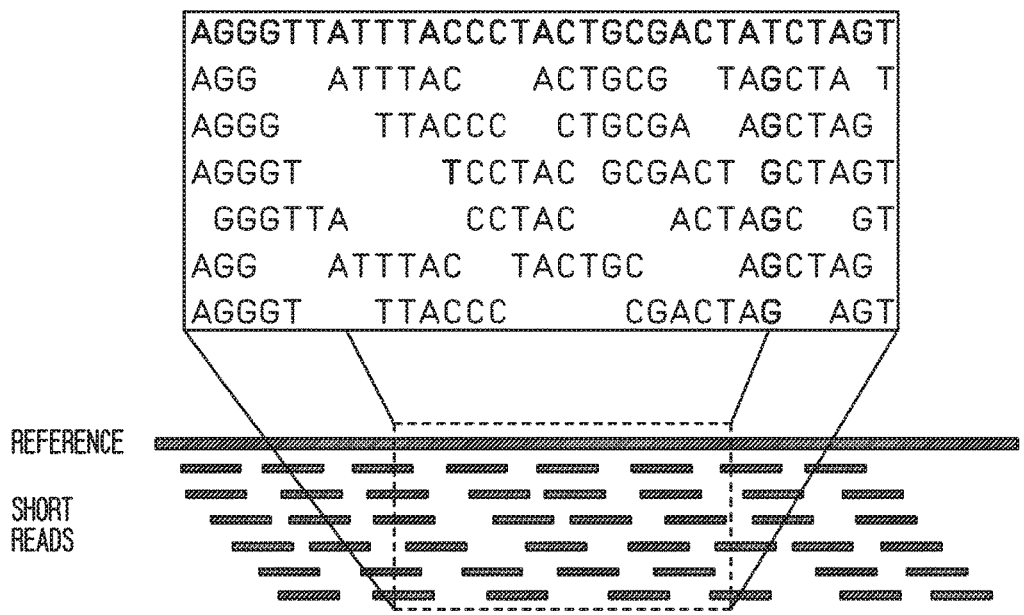
FIG. 8 illustrates an example set of short reads mapped to a section of a reference genome having a Sequence Listing of Sequence ID 1.

As mentioned above, the gene sequencing machines determine the nucleotide sequence of short DNA fragments, typically a few tens to hundreds of bases, called "short reads", derived from randomly fragmenting many copies of the genome of one organism for which a "reference" genome sequence is already known. In these cases, the first step in the data analysis pipeline is the short read mapping problem: determining the location in the reference genome to which each read maps best. The problem is technically challenging for two reasons. First, speed is important simply due to the volume of data. For example, in human genetic studies, mapping a billion reads from one subject to the human reference genome is routine. Second, the achieved sensitivity of the algorithm, which is the ability to successfully map sequences that are not completely identical to the reference, is an important consideration. These differences exist both because of technical errors in the sequencing machines (a frequent and uninteresting case) and because of genetic differences between the subject and the reference genome. The latter case is rarer and much more interesting—indeed it may be the entire purpose of the experiment, as it may reveal the cause of some genetic disease or a cancer-related mutation. The cases are distinguishable because the sequencer errors are random while the genetic differences are not. Hence many mapped reads that consistently exhibit a difference with respect to the reference at a particular locus signal a genetic change, whereas occasional scattered differences are probably errors. This also drives the desire for more and more reads, since more data gives more accurate variant-calling. FIG. 8 shows an example set of short reads mapped to a section of the reference genome and examples of both types of differences (sequencing errors and genetic variations). The highlighted "T" is a sequencing error, whereas the highlighted "G" is a genetic variation.

The representative embodiments utilize the fact that individual genomes differ only slightly, meaning it is likely that one or more subsequences of a short read will exactly match the reference genome. These subsequences are referred to as "seeds". An index of the reference genome is compiled first, which maps every seed that occurs in the reference genome to the locations where they occur. To align a short read, all the seeds in the read are looked up in the index, which yields a set of candidate alignment locations ("CALs"). The short read is then scored against the reference at each of these CALs, such as by using an FPGA 150, 160, 170 implementation of the Smith-Waterman string-matching algorithm, to provide a likelihood that the short read matches the reference location in the vicinity specified by the CAL. The candidate location with the highest score, or several candidate locations with comparatively high scores, is or are chosen as the alignment location for a short read.

A representative implementation uses seeds with 22 base-pairs, short reads with 76 base-pairs, and 2 bits per base encoding, but these are parameters which can be readily changed, and are provided solely for purposes of explanation.

Figure 9:
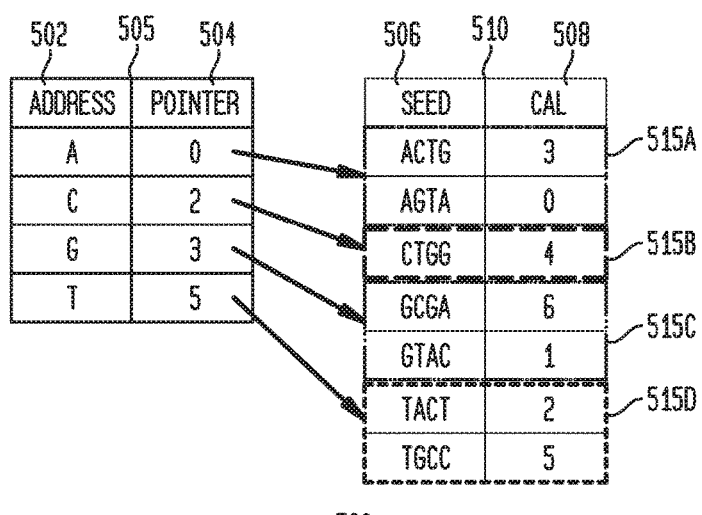
FIG. 9 is a flow diagram illustrating an exemplary or representative reference genome index generation method embodiment for an accelerated short read mapping configurable logic (FPGA) embodiment.

FIG. 9 is a diagram illustrating an exemplary or representative reference genome index 500 embodiment for an accelerated short read mapping configurable logic (FPGA) embodiment. A pre-compiled index 500 is used to map seeds of a short read to locations in the reference genome where the seed occurs. Highly novel, the reference genome index 500 is implemented using two tables, comprised of a pointer table 505 and a CAL table 510. The pointer table 505 is directly indexed using only a portion of the seed. This means that many seeds map to each entry of the pointer table 505. The CALs for these seeds are stored along with the corresponding seed as a list in a second table called the CAL table 510. The pointer table 505 is an array of pointers to the start of hash table (discussed below) groupings (or "buckets") 515 in the CAL table 510. The example illustrated in FIG. 9 is constructed for the reference AGTACTGCGA. Each entry in the pointer table 505 contains address bits 502 of the seed (described in greater detail below) and a pointer 504 to this list in the CAL table 510 along with the size of the list. Each CAL table 510 entry includes the key bits 506 (also described in greater detail below) and at least one CAL 508 entry. To look up the CALs for a seed, the pointer table 505 is consulted to find the beginning and end of the relevant grouping 515 (or "bucket") in the CAL table 510, illustrated as CAL table groupings (or buckets) 515A, 515B, 515C, and 515D. Each CAL table grouping or bucket 515 is searched for the CALs associated with the seed that provided the pointer into the selected CAL table grouping or bucket 515. Thus, looking up the CALs for a seed takes two memory 190 (DRAM) reads, one for retrieving information from the pointer table 505, and another to bring in the actual CAL table bucket 515 to be searched.

Figure 10:
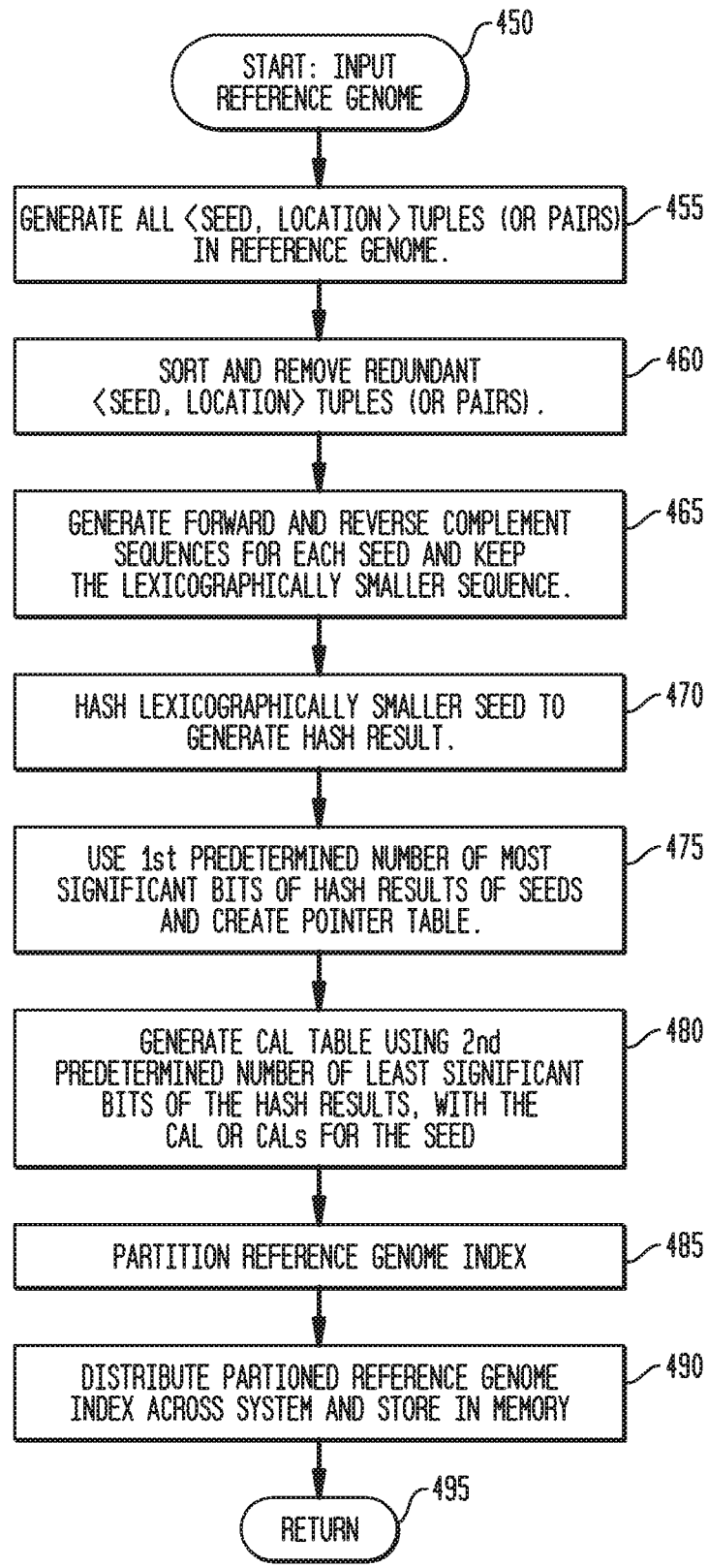
FIG. 10 is a diagram illustrating an exemplary or representative reference genome index embodiment for an accelerated short read mapping configurable logic (FPGA) embodiment.

FIG. 10 is a flow diagram illustrating an exemplary or representative reference genome index generation method embodiment for an accelerated short read mapping configurable logic (FPGA) embodiment. This method generates an index of the reference genome (or other similar data for analysis). As the reference genome index which is thereby created may be used repeatedly for every sample to be mapped, it is illustrated as a flow diagram for software implementation in a host computing system 105, and those having skill in the art will recognize that the reference genome index generation may be implemented anywhere within the system 100, 200, 300, 400, such as in the host computing system 105, or using any of the FPGAs 150, 160, 170.

Beginning with start step 450, the reference genome data is input to the host computing system 105. To compile the index for a reference genome, the data for the reference genome is examined, and a list of all the <seed, location> pairs in the genome is generated, step 455. This list is then sorted by seed, and seeds occurring too frequently in the reference genome are removed, step 460. Removing these abundant seeds avoids aligning reads to repetitive regions of the reference genome without negatively affecting the quality of the alignments. For example, the BFAST default level may be utilized, by removing seeds that occur more than 8 times in the reference genome.

In representative embodiments, the index also addresses and accounts for the problem that a short read might come from either the forward or reverse complement strand of the double-stranded DNA. There are several options for mapping reads to both the forward and the reverse complement strands. The first option is to index only the forward reference strand, and lookup both the short read and its reverse complement in the index of the forward genome. This solution doubles the number of reads to be mapped and would thus double the runtime. The second option is to index both the forward and the reverse complement genomes. Looking up the short read in this index would find the CALs for both the forward and the reverse complement genome.

However, this index would require approximately double the memory footprint as compared to an index for just the forward reference.

Instead, for the representative embodiments, each seed has two entries in an index constructed for both the forward and reverse complement genomes; in step 465, one entry is generated for the forward strand and one entry is generated for the reverse complement strand, but these entries have exactly the same location. Thus, in representative embodiments, also in step 465, only one seed entry is kept, and a bit is added that indicates whether it is the entry for the forward or the reverse strand. More specifically in step 465, when creating the index, the lexicographically smaller of the forward and the reverse complement seeds is retained and added to the index, e.g., "A" is lexicographically smaller than C, G, and T, "G" is lexicographically smaller than T but "lexicographically greater than A and C, G, etc. (An exception may be made for seeds that are their own reverse complement. In this case both the forward and reverse complement seed may remain in the CAL table.) This has further implications for subsequent read mapping, as described below.

One problem that arises when deterministically keeping the lexicographically smaller seed is a non-uniform distribution of the CALs in the CAL table 510 buckets 515. Since the lexicographically smaller version of the seed, we will tend to have more seeds that begin with "A" than seeds that begin with "T". This bias would cause the CAL table buckets 515 towards the beginning of the CAL table 510 to contain many more CALs than buckets 515 at the end of the CAL table 510. To address this issue, CALs are redistributed throughout all CAL table buckets 515 during the construction of the index by hashing the lexicographically smaller seed before adding it to the CAL table 510, step 470, to form a hash result. We hash the seeds using a 1-1 hash function on the 44-bit seed. We then use the most significant (30 in this case) bits of the hashed seed result to address and create the pointer table, step 475. The remaining (14) bits, which are sufficient to identify the seed, are stored amongst the CALs in the CAL table 510, and the CAL table 510 is generated, step 480. This produces a more uniform distribution of CALs through all CAL table buckets 515, and results in much more efficient and faster short read mapping. During the mapping phase, the same hash on the lexicographically smaller seed is performed before accessing the pointer table 505 and CAL table 510, as described in greater detail below. An example of a fully constructed reference genome index 500 for the reference string AGTACTGCGA is illustrated in FIG. 9.

The reference genome index 500 may then be partitioned as an option, step 485, as for distribution among FPGAs 150, 160, 170, step 490, thereby providing for each FPGA 150, 160, 170 to perform short read mapping against a portion of the reference genome stored in a memory 190, and the reference genome index generation method may end, return step 495. The partitioned index may be stored in host system memory 120, for example, with the host CPU 110 configuring the DMA engines of the FPGAs 150, 160, 170, as discussed above, which may then obtain the index 500 data from the host system memory 120 for use in the short read mapping and store it in memory 190. This distribution of the reference genome index 500 and the reference genome sequence is only required to be performed once for as long as the mapping application is to be performed, as multiple sets short reads are to be compared against the same reference genome sequence using the same reference genome index 500.

Figure 11:
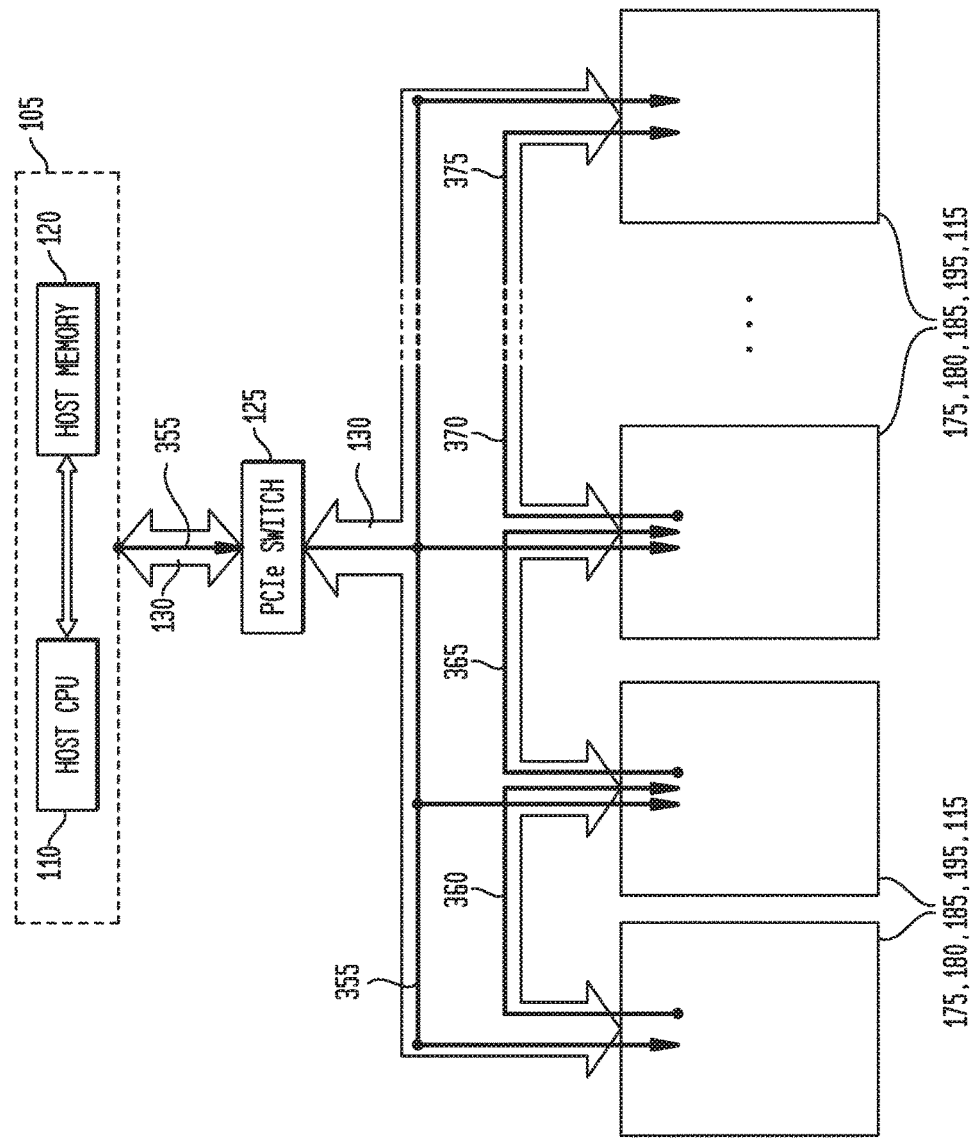
FIG. 11 is a block diagram illustrating an exemplary or representative data path for a data partition in a pipelined system embodiment.

FIG. 11 is a block diagram illustrating an exemplary or representative data path for a data partition in a pipelined system embodiment, and may utilize any of the computing modules 175, 180, 185, 195, 115. To improve the performance of the system 100, 200, 300, 400, the reference genome index 500 (and in representative embodiments, also the reference genome sequence) is or are partitioned across multiple memories 190, both within each computing module 175, 180, 185, 195, 115 and across multiple computing modules 175, 180, 185, 195, 115, to allow concurrent memory operations and reduce the memory footprint required per node in the system 100, 200, 300, 400. To partition the reference genome index 500 N ways, both the pointer table 505 and the CAL table 510 are partitioned by the first $\log_2$ (N) bits of the seed (after the seed has been hashed). For example, when partitioning two ways, seeds in the index that begin with an A or C go into the index for partition 0, and seeds beginning with G or T go into the index for partition 1. Portions of the reference genome sequence also may be correspondingly partitioned, or the entire reference genome sequence may be stored for use in evaluating the various CALs, with the latter case typically implemented. This partitioning typically extends across multiple memories 190 on multiple computing modules 175, 180, 185, 195, 115 with corresponding FPGAs 150, 160, 170, and may be performed as described above by the host CPU 110 configuring the DMA engines of the FPGAs 150, 160, 170, to read or otherwise obtain the corresponding partition from the host memory 120. This partitioning is illustrated in FIG. 11 by data path 355 from the host computing system 105 through the PCIe switch 125 and to each of the computing modules 175, 180, 185, 195, 115.

FPGAs 150, 160, 170 stream each short read through each of the reference genome index 500 partitions, both within any given computing modules 175, 180, 185, 195, 115, and between multiple computing modules 175, 180, 185, 195, 115, such as in a sequential or "daisy chaining" manner. For example, the best CAL determined for a selected short read based on a first partition will be evaluated again based on a next partition (until all partitions have been examined), and it may continue to be the best CAL or may be replaced by another CAL having a higher ranking or score in the next partition.

For each partition, the FPGA 150, 160, 170 looks up only those seeds that occur in its partition of the reference genome index 500. Using the example above with two partitions, a seed beginning with an A will only be looked up by the FPGA 150, 160, 170 having partition 0 of the reference genome index 500 stored in its corresponding memory (memories) 190 on its computing module 175, 180, 185, 195, 115. For each partition, the FPGA 150, 160, 170 collects the CALs for the short read and typically performs a Smith-Waterman comparison to the reference genome sequence. When finished, the FPGA 150, 160, 170 transfers the short read data along with the best alignment and score data to the next partition, which may be on the same computing module 175, 180, 185, 195, 115 or on a next computing module 175, 180, 185, 195, 115, using the data transfer (communication) methodology described above, with the latter case being illustrated in FIG. 11 by sequential data paths 360, 365, 370, 375 from one computing module 175, 180, 185, 195, 115 to another, next computing module 175, 180, 185, 195, 115. Using each partition, the FPGAs 150, 160, 170 update the best alignment and score in turn, with the FPGA 150, 160, 170 of the last partition producing the final best alignment and score, which may be returned to the host computing system 105 through the PCIe switch 125 or another FPGA 150, 160, 170 for any additional processing, such as assembling the complete sequence of the genome under analysis, for example and without limitation.

This aggregation is accomplished by creating a daisy-chain of the partitions using PCIe lines 130 for communication. For a selected partition, an FPGA 150, 160, 170 replaces the best alignment information on the short read stream if it aligns that short read with a higher score than the current best alignment score. Short reads are passed along the daisy chain between FPGAs 150, 160, 170 without the need for host CPU 110 control. The host computing system 105 simply needs to send short reads to the first FPGA 150, 160, 170 in the chain and receive results from the last FPGA 150, 160, 170 in the chain.

For example, each read requires 32 B of data to be streamed through the system 100, 200, 300, 400. Therefore, the total amount of data that must be streamed through the chain for 50 million reads is 1.5 GB. Gen2 x8 PCIe, which has a maximum sustained bandwidth of 3.2 GB/s, requires about 0.5 seconds to stream all the data for 50 million reads. Since the network is full duplex, reads can be streamed to the first FPGA 150, 160, 170 and results streamed from the last FPGA 150, 160, 170 concurrently.

The human genome typically requires an index of approximately 22 GB plus the reference genome sequence data for each partition. By partitioning the index across eight computing modules 175, 180, 185, 195, each of which may have four or more GB of DDR3 DRAM (for a memory 190), the entire reference genome index 500 and reference data are easily stored. For example, each partition contains 0.25 GB of the pointer table, 0.77 GB of the reference data, and approximately 2.5 GB of the CAL table.

In a first representative embodiment, the entire reference genome sequence is stored in memory 190 with each partition. Since the partitioning is not done by section of the genome, a short read may be aligned against the same reference bucket in multiple partitions. Inefficiency can be avoided by seeding the CAL filter (542, described below) at the beginning of each short read with all of the CALs that have previously been aligned for that short read. This increases the data passed between partitions, but greatly reduces the number of Smith-Waterman comparisons.

An early system 100, 200, 300, 400 was utilized for initial verification of the methodology of this disclosure, using a plurality of M-503 boards available from Pico Computing, Inc. Each M-503 contains a Xilinx Virtex-6 LX240T FPGA. It uses Gen2 x8 PCIe for external communication and contains 2x4 GB DDR3 SODIMMs running at 400 MHz. The M-503 module connects to an EX-500 backplane, which plugs into a motherboard x16 PCIe slot. Three M-503s can plug into the EX-500 backplane, and they are connected together using a full-duplex x8 switched PCIe network. Eight EX-500s can plug into a motherboard, allowing up to 24 M-503s in a chassis. M-503s can send and receive traffic external to the EX-500 backplane using full-duplex Gen2 x16 PCIe.

An exemplary mapping utilized three ports to the memory 190 (DDR3) system, operating on a 200 MHz clock. Each access to the memory 190 system, whether to the pointer table 505, CAL table 510, or reference genome data, is a random address, with pipelining and out-of-order memory accesses utilized to attain the high memory bandwidth for these memory accesses. For example, the M-503 uses x64 DDR3 SODIMMs, which return at least 256 bits of data per read burst.

In an example system 100, 200, 300, 400, the pointer table 505 data is efficiently packed into these 256-bit boundaries. Each CAL table 510 entry requires 64 bits, for a total of four entries per 256-bit boundary of the DRAM. The reference is packed two bits per base, yielding 128 reference bases per DRAM boundary. After filtering out seeds that appear more than eight times in the reference genome, the total CAL table 510 contains 2.44 billion entries, which requires 19.5 GB of DRAM to store the CAL table 510. The packed pointer table 505 requires 2 GB of memory 190 and the reference genome is stored in 0.77 GB of memory.

Figure 12:
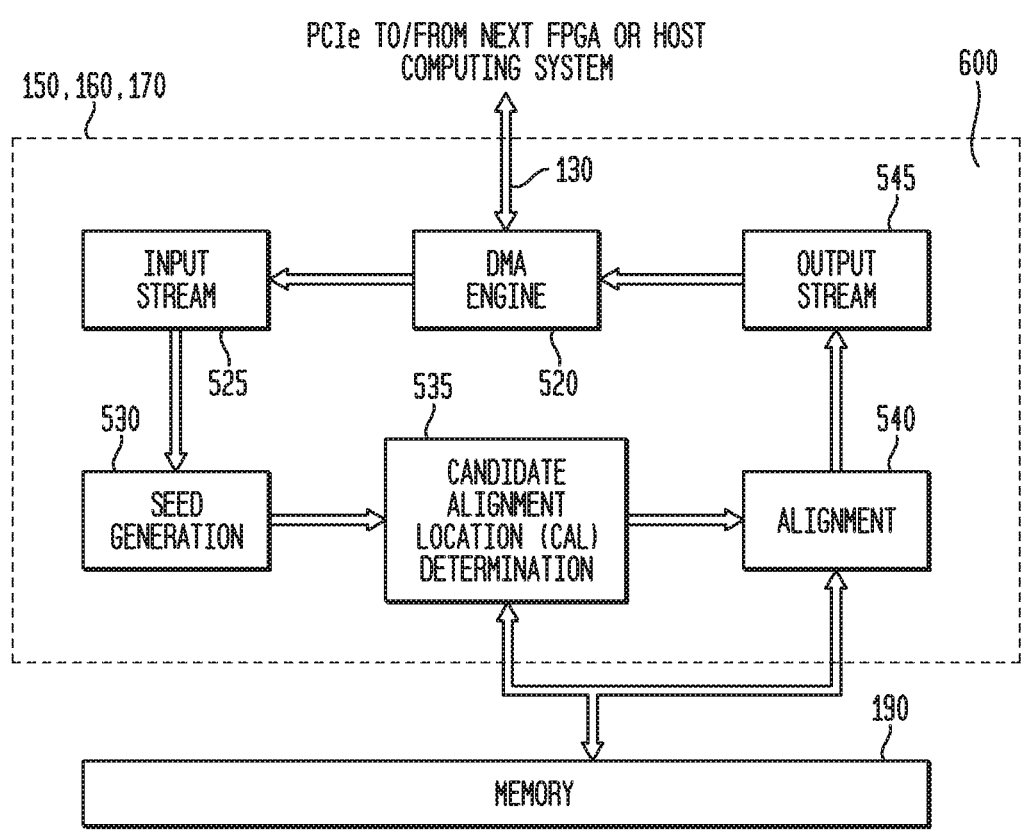
FIG. 12 is a system configuration block diagram illustrating an exemplary or representative accelerated short read mapping FPGA configuration embodiment.

FIG. 12 is a system configuration block diagram illustrating an exemplary or representative accelerated short read mapping FPGA configuration embodiment 600, which may be implemented using any of the FPGAs 150, 160, 170 and memory (or memories) 190 (such as DDR3) on any of the computing modules (boards or cards) 175, 180, 185, 195, 115. More specifically, each of the various "configuration blocks" described herein are one or more configurations of an FPGA 150, 160, 170, and these one or more configurations may be loaded into the FPGA 150, 160, 170 as described above. In addition, any of the data transfers between and among the FPGAs 150, 160, 170 may be performed as described above, such as for transferring data between partitions, for example and without limitation.

The reference genome index 500, or a part or partition of the reference genome index 500 (when partitioned), has been stored in memory 190, which may be comprised of several memory ICs. In addition, the corresponding reference genome sequence or part of the reference genome sequence is also stored in memory 190, for use in subsequent alignment processing.

As illustrated in FIG. 12, the FPGA configuration embodiment 600 comprises a DMA engine 520 (as discussed above), which provides (to the other modules or to the memory 190) an input data stream 525 having one or more short reads from a sample for analysis (along with its then current best candidate alignment location) received from the PCIe communication lines 130 (e.g., a short read sample from host memory 120), and which provides or transmits an output data stream 545 (having the data for the currently best candidate location of the short read in the reference genome) on the PCIe communication lines 130, which may then be provided to another FPGA configuration embodiment 600 for additional processing (to further determine the best reference genome location for the short read) or to the host computing system 105 (as the best reference genome location for the short read). The FPGA configuration embodiment 600 further comprises the configurations which perform the short read mapping of a sequenced DNA sample to the reference genome, namely, a seed generation configuration block 530, a candidate alignment location (CAL) determination configuration block 535, and an alignment location selection configuration block 540. Each of the seed generation configuration block 530, candidate alignment location (CAL) determination configuration block 535, and alignment location selection configuration block 540 are illustrated in greater detail in FIGS. 13-15.

Figure 13:
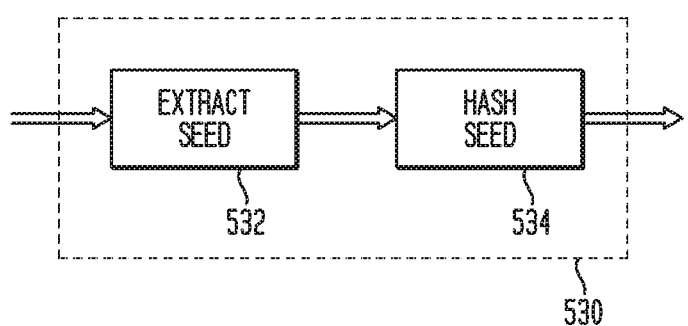
FIG. 13 is a system configuration block diagram illustrating in greater detail an exemplary or representative seed generation configuration block 530 for an accelerated short read mapping configurable logic (FPGA) embodiment.

The input data stream 525 may be considered to have a plurality of "queries" which are to be mapped, i.e., having one or more short reads from a sample for analysis, along with its then current best candidate alignment location. This input data stream 525 is input into seed generation configuration block 530, which typically selects one short read (i.e., one query) at a time. The first step in mapping reads to the reference genome is to extract all seeds from each short read, which may be done using a shift register, for example and without limitation. As mentioned above, a representative seed length is 22 bases. As illustrated in FIG. 13, the seed generation configuration block 530 extracts all seeds from the short read (query), seed extraction configuration block 532. As it is unknown whether the short read (query) was from a forward or reverse complement strand of DNA, the seed generation configuration block 530 also generates a reverse complement of each seed, so that both forward and reverse complement seeds are provided, and the lexicographically smaller of the two (forward and reverse complement) is retained (matching the process to build the reference genome index). A hash (the same hash used in generating the reference genome index 500, described above) is then computed for the retained (lexicographically smaller forward or reverse complement seed), using hash seed generator configuration block 534, which evenly distributes accesses to the reference genome index 500 in memory 190. Each hashed seed (along with an identification of the query (short read) to which it belongs, is then provided to the candidate alignment location (CAL) determination configuration block 535.

Figure 14:
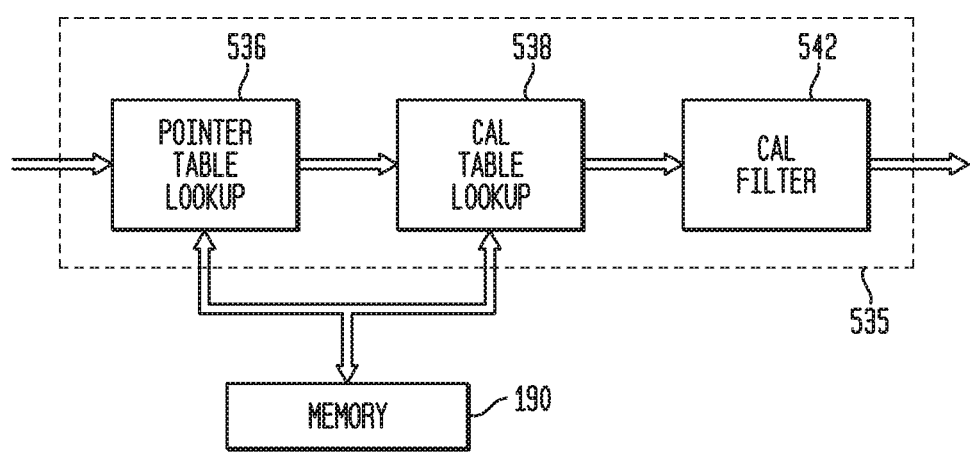
FIG. 14 is a system configuration block diagram illustrating in greater detail an exemplary or representative candidate alignment location (CAL) determination configuration block 535 embodiment for an accelerated short read mapping configurable logic (FPGA) embodiment.
Figure 16:
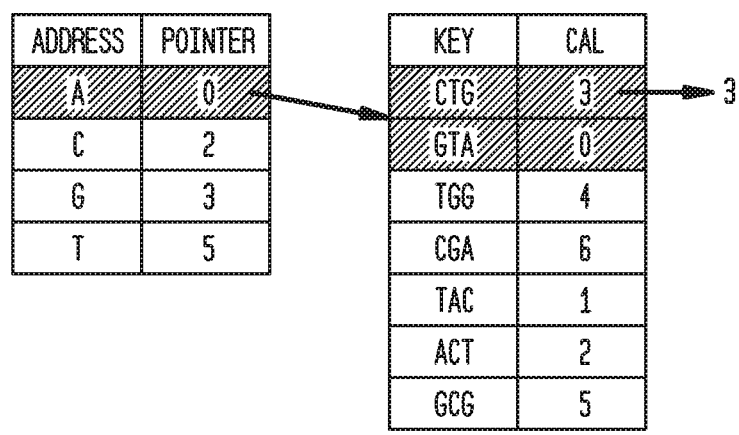
FIG. 16 illustrates an exemplary or representative access to a reference genome index using a hashed seed with the visited entries of the pointer table and CAL table highlighted.

As illustrated in FIG. 14, the candidate alignment location (CAL) determination configuration block 535 performs two lookups in memory 190 for each hashed seed: a pointer table (505) lookup, using pointer table lookup configuration block 536, and a CAL table (510) lookup, using CAL table lookup configuration block 538. To find CALs for a hashed seed, the most significant bits (MSB) of the seed, referred to as the address bits, are utilized by the pointer table lookup configuration block 536 to access the pointer table 505 and obtain the corresponding pointer to the correct CAL table bucket 515 in the CAL table 510. The remaining bits (least significant bits (LSB)) of the hashed seed are referred to as the key bits. CAL table lookup configuration block 538 performs a linear scan through the CAL table bucket 515, and CALs of entries with key bits matching those of the current hashed seed are added to the set of CALs for the current short read (query). This second memory 190 access then provides all the CALs for the current short read, which are accumulated and queued. An example index access for a hashed seed is illustrated in FIG. 16 with the visited entries of the pointer table 505 and CAL table 510 highlighted.

Those having skill in the art will recognize that there are many alternatives to using such address bits (MSB) and key bits (LSB) for accessing the pointer table 505 and CAL table 510. For example, such MSB and LSB accessing could be reversed, or a random selection of bits from the seed could be utilized to access the pointer table 505 and CAL table 510, for example and without limitation. All such variations are considered equivalent and within the scope of the disclosure.

Candidate alignments of seeds in a reference genome using an index have been obtained, and these are locations, which give the location of the start of the seed, are converted to the candidate location of the read containing that seed. This normalization is performed by subtracting from the CAL the offset of the start of the seed with respect to the start of the short read. For example, if the seed starting at the third base of the short read finds a CAL of 34, we offset that CAL back to the start of the short read, location 32. This normalization gives us the exact location of the read in the reference if we assume that the genome being sequenced has no insertions or deletions with respect to the reference genome. To allow for up to N insertions and deletions, we compare the short read to a section in the reference genome starting N bases before start of the short read's CAL (given by the index) and ending N bases after the end of the short read. This is performed by the CAL table lookup configuration block 538.

To simplify the hardware, the reference genome is divided into reference blocks whose size is determined by the size of a single read from memory 190 (DRAM). All CALs are converted to the start of the reference block that contains the CAL, and the short read is aligned to the reference starting at the beginning of a block. This increases the size of the reference sequence compared against the short read, but the increase in time for this comparison is offset by much simpler hardware.

Many CALs are collected for a short read when looking up its seeds in the index. However, many of these CALs will refer to the same place in the reference, and the short read only needs to be compared once at each of these locations. For example, a representative system 100, 200, 300, 400 with 22-base seeds in 76-base short reads does 55 (76−22+1) index lookups, so an exact match to the reference will find the same CAL 55 times. The accumulated CALs are then filtered to remove any redundancies, using CAL filter configuration block 542, and the filtered list of CALs are provided to the alignment location selection configuration block 540. More specifically, repeat CALs are removed from the set for a short read by saving the CALs, along with their reverse complement bit, in a hash table (used to implement the CAL filter 542) as they are processed. If an entry already appears in the CAL filter table, it is ignored. Each entry also stores a sequence number associated with each short read. This is incremented for each new short read, which implicitly clears the CAL filter 542 hash table between short reads. For example, a CAL filter configuration block 542 may be implemented using block RAMs on the FPGA 150, 160, 170 as a hash table with 1024 entries. CALs are therefore hashed to 10 bits to determine the target entry of the table.

Figure 15:
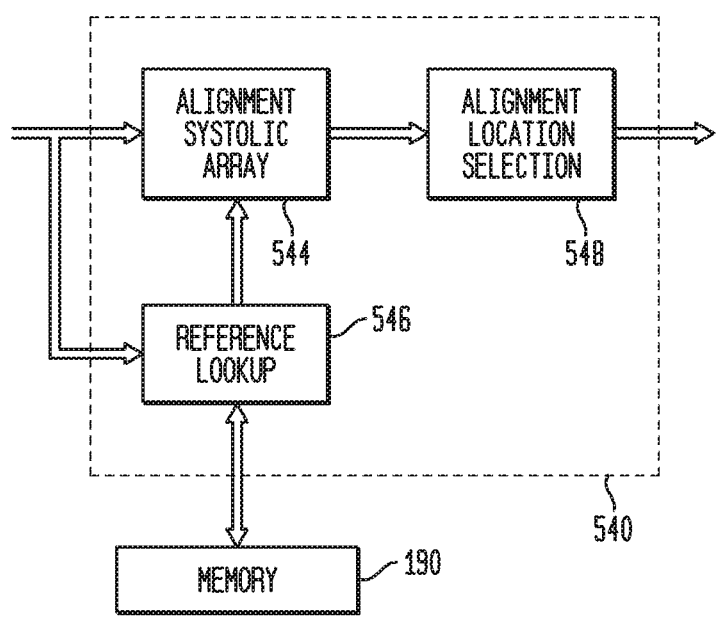
FIG. 15 is a system configuration block diagram illustrating in greater detail an exemplary or representative alignment location selection configuration block 540 for an accelerated short read mapping configurable logic (FPGA) embodiment.

Referring to FIG. 15, an alignment location selection configuration block 540 may be considered to comprise three configuration blocks, a reference lookup configuration block 546, an alignment systolic array configuration block 544, and an alignment location selection (or score tracking) configuration block 548. As discussed in greater detail below, in a representative embodiment, multiple alignment systolic array configuration blocks 544 are implemented and operate in parallel, and data for alignment is provided to each in a round-robin manner. For each CAL received from the CAL filter configuration block 542, the reference lookup configuration block 546 locates that section of the reference genome in memory 190, and provides a reference genome data read for the candidate location, aligned to the read size, typically 128 bases (256 bits), and including any predetermined offset amount (as discussed above), i.e., generating a gene sequence data read from the reference genome beginning with the candidate location minus the offset, and continuing to the candidate location plus the query length (the short read length) plus the offset.

The reference gene sequence data read, for each CAL, from the reference lookup configuration block 546 is then provided to the alignment systolic array configuration block 544 which will compare the short read to the gene sequence data read for the selected CAL, base-by-base, and providing a ranking or score for that selected CAL for the selected short read, which is a likelihood of the short read matching the reference genome sequence in the vicinity of the location which was specified by the selected CAL, computed using a base-by-base comparison of the short read with the corresponding section of the reference genome sequence (i.e., the sequence beginning with the candidate location minus the offset, and continuing to the candidate location plus the query length (the short read length) plus the offset). In a representative embodiment, the alignment systolic array configuration block 544 of the FPGA 150, 160, 170 implements a Smith-Waterman computation. In another representative embodiment, the alignment systolic array configuration block 544 implements an affine gap model computation. Both of these are discussed in greater detail below.

Instead of doing local alignment of a short read against the reference, or global alignment of the short read and reference, we globally align the short read against a local section of the reference. In other words, we want to score the alignment of the entire short read to a subsequence of the reference genome, as described above.

Figure 17:
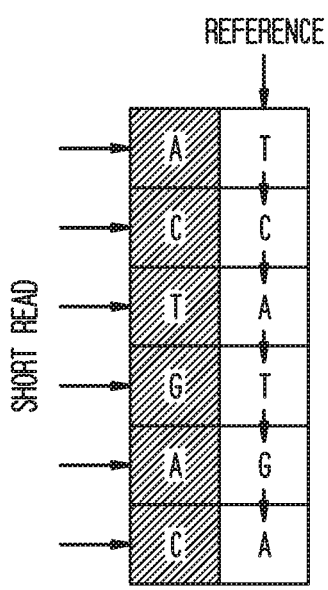
FIG. 17 illustrates an exemplary or representative systolic array for a Smith-Waterman computation.

In the first embodiment, one or more Smith-Waterman engines are implemented as a systolic array, as shown in FIG. 17, using alignment systolic array configuration block 544 of an FPGA 150, 160, 170. Each cell computes the value of one entry in the 2D Smith-Waterman matrix each clock cycle. An array of cells computes the anti-diagonal of the Smith-Waterman matrix in parallel. In other words, the systolic array enables each base of the short read to be scored against a base of the reference genome sequence simultaneously, which changes the runtime of the Smith-Waterman computation from $O(M \times N)$ for M length reference and N length short read to $O(M+N)$.

This CAL score or ranking output from the alignment systolic array configuration block 544, then, is a likelihood of the short read matching the reference genome sequence around the location (i.e., including the offsets mentioned above) which was specified by the selected CAL, computed using a base-by-base comparison of the short read to the reference genome sequence. Such a likelihood (score or ranking) is generated for each CAL for the short read, for the selected partition of the reference genome index 500.

The output of the alignment systolic array configuration block 544 is then a score or a ranking of each selected CAL, based upon a base-by-base comparison of the selected short read to the reference genome sequence at the location specified by the selected CAL. As a result, for each short read, a plurality of CAL scores or rankings are provided by the alignment systolic array configuration block 544 to the alignment location selection (or score tracking) configuration block 548. As previously mentioned, a previously determined (currently best) CAL and CAL likelihood score or ranking for a selected short read was provided by any previous FPGA 150, 160, 170 which mapped the same short read to a selected partition in the pipeline of FPGAs 150, 160, 170, or if no previous partition was analyzed for the short read, then a score or ranking of zero. The alignment location selection (or score tracking) configuration block 548 implements a maximum (MAX) selection function, comparing the best CAL likelihood score or ranking provided in the current partition by the alignment systolic array configuration block 544 with the CAL likelihood score or ranking of any CAL provided from another partition, and in a first embodiment, selects the CAL for the short read having the highest score or ranking, which may be either the best CAL provided by the alignment systolic array configuration block 544 or from the alignment using a previous partition. In a second embodiment, the alignment location selection (or score tracking) configuration block 548 may select one or more CALs for the short read having the higher or greater scores or rankings. As a result, as a short read is analyzed in each partition, the output of each alignment location selection (or score tracking) configuration block 548 for each partition is the currently best overall CAL for the selected short read (or, for the second embodiment, a group of the better CALs for the selected short read).

This output of the currently best overall CAL (or group of the better CALs) for the selected short read from the alignment location selection (or score tracking) configuration block 548 either is then provided as input to the next stage in the partition sequence (which may be the next partition to be analyzed by the current FPGA 150, 160, 170 for the short read or which may be a next FPGA 150, 160, 170 in the partition sequence) or, when the alignment location selection (or score tracking) configuration block 548 is the last alignment location selection (or score tracking) configuration block 548 among all the partitions, is provided as the final selection of the best overall location (or group of locations) for the selected short read in the reference genome sequence. For the latter case, the output of the best overall location (or group of locations) for the selected short read in the reference genome sequence may be routed as data to either the host computing system 105 or to another FPGA 150, 160, 170, e.g., for further processing to determine the entire sequence of the sample genome (which provided the plurality of short reads under current analysis).

Due to the many levels of logic in the unit cell of the systolic array, the Smith-Waterman system may be run at a slower clock, e.g., a 125 MHz clock. One benefit of the systolic array is the ability to pipeline the alignment of a single short read to multiple reference buckets, which reduces the runtime to approximately equal the length of the reference bucket (M), instead of the reference bucket plus the read length (M+N).

Reference data is packed to 256-bit boundaries in memory 190 (e.g., DDR3 DRAM), which should mean that 76 base reads can be aligned against 128 bases of the reference genome sequence. A short read alignment, however, may often cross the 256-bit boundary of the memory 190. Therefore, the short read is aligned to a 256-base (2×256 bits) section of the reference genome sequence. When aligning against a 256-base reference bucket, a single Smith-Waterman computation requires approximately 76+256=332 cycles. Since each computation takes so many cycles to complete, we multiple Smith-Waterman compute engines are instantiated in each FPGA 150, 160, 170, with the required computations performed in a round-robin manner among the instantiated compute units. An optimal number of Smith-Waterman engines to instantiate in the alignment systolic array configuration block 544 should be just enough to keep up with the pointer table, CAL table, and reference memory accesses.

In a second embodiment, the affine gap model is utilized, which scores long insertion or deletion chains different from short insertions and deletions. In this model, the cost to begin an insertion or deletion chain is higher than the cost to continue an insertion or deletion chain. This model allows for longer insertion and deletion chains to appear in the actual alignment, which can be more biologically accurate. However, this model requires that we store three copies of the 2D scoring array. The first copy is the similarity score, and the other two are the current insertion and deletion scores at each cell respectively.

When using the affine gap model, the score for a cell is computed by solving (3), where $\alpha$ is a positive value that is the gap-open penalty, $\beta$ is a positive value that is the gap-extension penalty, $E(i,j)$ is the current read gap score for cell $(i,j)$, $F(i,j)$ is the current reference gap score for cell $(i,j)$, $\sigma(S[i], T[j])$ is the positive or negative score from the similarity matrix for read base i and reference base j, and $V(i,j)$ is the final similarity score for cell $(i,j)$.

$$E(i, j) = \max \begin{cases} V(i, j-1) - \alpha \\ E(i, j-1) - \beta \end{cases} \quad (1)$$

$$F(i, j) = \max \begin{cases} V(i-1, j) - \alpha \\ F(i-1, j) - \beta \end{cases} \quad (2)$$

$$V(i, j) = \max \begin{cases} E(i, j) \\ F(i, j) \\ V(i-1, j-1) + \sigma(S[i], T[j]) \end{cases} \quad (3)$$

The matrix is computed by sweeping i from 1 to the length of the short read (N), and by sweeping j from 1 to the length of the reference (M) being compared. For example, the scoring matrix may utilize a set to +2, β to +1, and the similarity matrix a set such that matching bases are +2 and mismatching bases are −2; these settings, however, are readily changeable to any desired levels by a user. To guarantee that the short read is globally aligned to the local reference, the scoring matrices (V, E, and F) are initialized according to (4):

$$V(i, j) = \begin{cases} 0 & i = 0, 1 \le j \le M \\ -\alpha - (i-1) * \beta & 1 \le i \le N, j = 0 \end{cases} \quad (4)$$

An example of a fully aligned read and the backtracking process is illustrated in FIG. 18. This example shows the similarity score matrix for the global alignment of the short read to a local section of the reference. The short read matches the reference perfectly with the exception of a single base "A". Only the similarity matrix of the affine gap model is shown here, but the insertion and deletion matrices are included in the computation.

The results from using the system 100, 200, 300, 400 were substantial. For example, the system 100, 200, 300, 400 showed an improvement of 250x speed up in mapping time compared to the BFAST software, and a 31x speed up over the Bowtie software, a one to two orders of magnitude improvement. Comparing the time to map 50 million short reads using a selected implementation of the system 100, 200, 300, 400 (described above) versus BFAST and Bowtie, the system 100, 200, 300, 400 mapped 50 million 76-base reads in 34 seconds, with a 250x speedup over BFAST, which took 8,480 seconds (2 hours, 21 minutes, 20 seconds), and a 31x speedup over Bowtie, which mapped 50 million reads in 1,051 seconds (17 minutes, 31 seconds).

In addition to improvement in runtime, the system 100, 200, 300, 400 provided greater sensitivity compared to the prior art software implementations, and these sensitivity levels can be tuned. For example, the system 100, 200, 300, 400 was able to map 91.5% of 50 million short reads, compared to 80.2% provided by Bowtie which, moreover, unlike the system 100, 200, 300, 400, was unable to handle reads that differed from the reference genome by more than three bases. Even when using the "best" option while running Bowtie (which slows down the runtime), only 85.8% of the reads were mapped. The differences between the reference genome and reads are often the data of most interest in a next-generation sequencing experiment, perhaps identifying the location of a genetic variant responsible for a heritable disease. Thus, the increase in sensitivity afforded by the system 100, 200, 300, 400 is of considerable importance.

In addition, higher sensitivity may be realized by tuning the system 100, 200, 300, 400 by reducing the seed length, which is readily available as an alternative in the system 100, 200, 300, 400, and allows more CALs to be found per read, enabling more reads to be aligned with the reference genome sequence. This is significant both for determining high rates of genetic variation and for assembling reads using a genome from a related species. When testing species with high rates of genetic variation, or using the reference genome as a template for the assembly of reads from the genome of a closely related species, this option may be more important. Conversely, the prior art Bowtie software cannot be tuned to compete with the sensitivity of the system 100, 200, 300, 400.

Because of such significant acceleration, overall energy consumption is also reduced using the system 100, 200, 300, 400. For example, the system 100, 200, 300, 400 in an example mapping utilized only about 0.8% of the energy required for a BFAST system, and about 4.7% of the energy required for the Bowtie system. Again, an improvement of one to two orders of magnitude.

These results demonstrate the power of this FPGA short read mapping system 100, 200, 300, 400. This system 100, 200, 300, 400 is able to map reads to the full genome faster, while using significantly less energy than both of the two tested software tools. A two orders of magnitude speedup (250x) versus the BFAST software, and a one order of magnitude speedup (31x) versus the lower-quality Bowtie software running on two quad-core Intel Xeon processors, has been demonstrated.

These improvements in system runtime help to enable research that was not possible before. For example, researchers can use this to study sequencing technologies with higher read error rates, which require a very large read depth during mapping. Similarly, this new technology of the present disclosure enables researchers to study larger genomes that may not have been possible before, such as barley (5.3 G bases). Also, this system 100, 200, 300, 400 can be tuned for the speed versus sensitivity trade-off, which enables researchers to study genomes with large genetic variation among the species.

The present disclosure is to be considered as an exemplification of the principles of the invention and is not intended to limit the invention to the specific embodiments illustrated. In this respect, it is to be understood that the invention is not limited in its application to the details of construction and to the arrangements of components set forth above and below, illustrated in the drawings, or as described in the examples. Systems, methods and apparatuses consistent with the present invention are capable of other embodiments and of being practiced and carried out in various ways.

Although the invention has been described with respect to specific embodiments thereof, these embodiments are merely illustrative and not restrictive of the invention. In the description herein, numerous specific details are provided, such as examples of electronic components, electronic and structural connections, materials, and structural variations, to provide a thorough understanding of embodiments of the present invention. One skilled in the relevant art will recognize, however, that an embodiment of the invention can be practiced without one or more of the specific details, or with other apparatus, systems, assemblies, components, materials, parts, etc. In other instances, well-known structures, materials, or operations are not specifically shown or described in detail to avoid obscuring aspects of embodiments of the present invention. In addition, the various Figures are not drawn to scale and should not be regarded as limiting.

Reference throughout this specification to "one embodiment", "an embodiment", or a specific "embodiment" means that a particular feature, structure, or characteristic described in connection with the embodiment is included in at least one embodiment of the present invention and not necessarily in all embodiments, and further, are not necessarily referring to the same embodiment. Furthermore, the particular features, structures, or characteristics of any specific embodiment of the present invention may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

It will also be appreciated that one or more of the elements depicted in the Figures can also be implemented in a more separate or integrated manner, or even removed or rendered inoperable in certain cases, as may be useful in accordance with a particular application. Integrally formed combinations of components are also within the scope of the invention, particularly for embodiments in which a separation or combination of discrete components is unclear or indiscernible. In addition, use of the term "coupled" herein, including in its various forms such as "coupling" or "couplable", means and includes any direct or indirect electrical, structural or magnetic coupling, connection or attachment, or adaptation or capability for such a direct or indirect electrical, structural or magnetic coupling, connection or attachment, including integrally formed components and components which are coupled via or through another component.

A CPU or "processor" 110 may be any type of processor, and may be embodied as one or more processors 110, configured, designed, programmed or otherwise adapted to perform the functionality discussed herein. As the term processor is used herein, a processor 110 may include use of a single integrated circuit ("IC"), or may include use of a plurality of integrated circuits or other components connected, arranged or grouped together, such as controllers, microprocessors, digital signal processors ("DSPs"), parallel processors, multiple core processors, custom ICs, application specific integrated circuits ("ASICs"), field programmable gate arrays ("FPGAs"), adaptive computing ICs, associated memory (such as RAM, DRAM and ROM), and other ICs and components, whether analog or digital. As a consequence, as used herein, the term processor should be understood to equivalently mean and include a single IC, or arrangement of custom ICs, ASICs, processors, microprocessors, controllers, FPGAs, adaptive computing ICs, or some other grouping of integrated circuits which perform the functions discussed below, with associated memory, such as microprocessor memory or additional RAM, DRAM, SDRAM, SRAM, MRAM, ROM, FLASH, EPROM or E²PROM. A processor (such as processor 110), with its associated memory, may be adapted or configured (via programming, FPGA interconnection, or hard-wiring) to perform the methodology of the invention, as discussed above. For example, the methodology may be programmed and stored, in a processor 110 with its associated memory (and/or memory 120) and other equivalent components, as a set of program instructions or other code (or equivalent configuration or other program) for subsequent execution when the processor is operative (i.e., powered on and functioning). Equivalently, when the processor 110 may implemented in whole or part as FPGAs, custom ICs and/or ASICs, the FPGAs, custom ICs or ASICs also may be designed, configured and/or hard-wired to implement the methodology of the invention. For example, the processor 110 may be implemented as an arrangement of analog and/or digital circuits, controllers, microprocessors, DSPs and/or ASICs, collectively referred to as a "processor", which are respectively hard-wired, programmed, designed, adapted or configured to implement the methodology of the invention, including possibly in conjunction with a memory 120.

The memory 120, 140, 190, which may include a data repository (or database), may be embodied in any number of forms, including within any computer or other machine-readable data storage medium, memory device or other storage or communication device for storage or communication of information, currently known or which becomes available in the future, including, but not limited to, a memory integrated circuit ("IC"), or memory portion of an integrated circuit (such as the resident memory within a processor 110), whether volatile or non-volatile, whether removable or non-removable, including without limitation RAM, FLASH, DRAM, SDRAM, SRAM, MRAM, FeRAM, ROM, EPROM or E²PROM, or any other form of memory device, such as a magnetic hard drive, an optical drive, a magnetic disk or tape drive, a hard disk drive, other machine-readable storage or memory media such as a floppy disk, a CDROM, a CD-RW, digital versatile disk (DVD) or other optical memory, or any other type of memory, storage medium, or data storage apparatus or circuit, which is known or which becomes known, depending upon the selected embodiment. The memory 120, 140, 190 may be adapted to store various look up tables, parameters, coefficients, other information and data, programs or instructions (of the software of the present invention), and other types of tables such as database tables.

As indicated above, the processor 110 is hard-wired or programmed, using software and data structures of the invention, for example, to perform the methodology of the present invention. As a consequence, the system and method of the present invention may be embodied as software which provides such programming or other instructions, such as a set of instructions and/or metadata embodied within a non-transitory computer readable medium, discussed above. In addition, metadata may also be utilized to define the various data structures of a look up table or a database. Such software may be in the form of source or object code, by way of example and without limitation. Source code further may be compiled into some form of instructions or object code (including assembly language instructions or configuration information). The software, source code or metadata of the present invention may be embodied as any type of code, such as C, C++, SystemC, LISA, XML, Java, Brew, SQL and its variations (e.g., SQL 99 or proprietary versions of SQL), DB2, Oracle, or any other type of programming language which performs the functionality discussed herein, including various hardware definition or hardware modeling languages (e.g., Verilog, VHDL, RTL) and resulting database files (e.g., GDSII). As a consequence, a "construct", "program construct", "software construct" or "software", as used equivalently herein, means and refers to any programming language, of any kind, with any syntax or signatures, which provides or can be interpreted to provide the associated functionality or methodology specified (when instantiated or loaded into a processor or computer and executed, including the processor 110, for example).

The software, metadata, or other source code of the present invention and any resulting bit file (object code, database, or look up table) may be embodied within any tangible, non-transitory storage medium, such as any of the computer or other machine-readable data storage media, as computer-readable instructions, data structures, program modules or other data, such as discussed above with respect to the memory 120, 140, 190, e.g., a floppy disk, a CDROM, a CD-RW, a DVD, a magnetic hard drive, an optical drive, or any other type of data storage apparatus or medium, as mentioned above.

Furthermore, any signal arrows in the drawings/Figures should be considered only exemplary, and not limiting, unless otherwise specifically noted. Combinations of components of steps will also be considered within the scope of the present invention, particularly where the ability to separate or combine is unclear or foreseeable. The disjunctive term "or", as used herein and throughout the claims that follow, is generally intended to mean "and/or", having both conjunctive and disjunctive meanings (and is not confined to an "exclusive or" meaning), unless otherwise indicated. As used in the description herein and throughout the claims that follow, "a", "an", and "the" include plural references unless the context clearly dictates otherwise. Also as used in the description herein and throughout the claims that follow, the meaning of "in" includes "in" and "on" unless the context clearly dictates otherwise.

The foregoing description of illustrated embodiments of the present invention, including what is described in the summary or in the abstract, is not intended to be exhaustive or to limit the invention to the precise forms disclosed herein. From the foregoing, it will be observed that numerous variations, modifications and substitutions are intended and may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

one or more field programmable gate arrays coupled to the one or more memory circuits, the one or more field programmable gate arrays configured to select a short read from the plurality of short reads; to extract a plurality of seeds from the short read, each seed comprising a genetic subsequence of the short read; for each seed of the plurality of seeds, to determine at least one candidate alignment location in the reference genome sequence to form a plurality of candidate alignment locations; for each candidate alignment location of the plurality of candidate alignment locations, to determine a likelihood of the short read matching the reference genome sequence in the vicinity of the candidate alignment location; and to select one or more candidate alignment locations, of the plurality of candidate alignment locations, having the currently greater likelihoods of the short read matching the reference genome sequence.

2. The system of claim 1, wherein the one or more field programmable gate arrays are further configured to use a selected seed, of the plurality of seeds, to access a reference genome index to determine the at least one candidate alignment location.

3. The system of claim 2, wherein the reference genome index is partitioned over the one or more memory circuits to form a plurality of reference genome index partitions.

4. The system of claim 2, wherein the one or more field programmable gate arrays are further configured to select one or more first candidate alignment locations having the currently greater one or more first likelihoods from a first partition of the plurality of reference genome index partitions; to compare the one or more first likelihoods with one or more second likelihoods of one or more second candidate alignment locations from a second partition of the plurality of reference genome index partitions; and to select the one or more candidate alignment locations having the currently greater likelihoods of the one or more first and second likelihoods.

5. The system of claim 4, wherein the one or more field programmable gate arrays are further configured to transfer

It is claimed:

1. A system for acceleration of short read mapping to a reference genome sequence for genomic analysis, the system coupled to a host computing system, the system comprising:

one or more memory circuits storing a plurality of short reads and a reference genome sequence, each short read comprising a sequence of a plurality of genetic bases; and the one or more candidate alignment locations having the currently greater likelihoods for mapping of the short read using a next, third partition of the plurality of reference genome index partitions.

6. The system of claim 2, wherein the one or more field programmable gate arrays are further configured to hash the selected seed and use the hashed seed to access the reference genome index.

7. The system of claim 6, wherein the one or more field programmable gate arrays are further configured to generate a forward sequence and a reverse complement sequence for the selected seed; to determine which of the forward sequence or the reverse complement sequence is lexicographically smaller; to hash the lexicographically smaller sequence to produce a hash result; and to use the hash result as the hashed seed to access the reference genome index.

8. The system of claim 2, wherein the reference genome index comprises a pointer table and a candidate alignment location table.

9. The system of claim 8, wherein each entry of the pointer table comprises a first predetermined number of the most significant bits of a hashed seed sequence and a pointer to a corresponding part of the candidate alignment location table.

10. The system of claim 9, wherein each entry of the candidate alignment location table comprises a second predetermined number of the least significant bits of a hashed seed sequence and a corresponding candidate alignment location.

11. The system of claim 10, wherein the one or more field programmable gate arrays are further configured to use the first predetermined number of the most significant bits of the selected hashed seed to access the pointer table to obtain a corresponding pointer; and to use the corresponding pointer and the second predetermined number of the least significant bits of the selected hashed seed to determine the candidate alignment location.

12. The system of claim 2, wherein the host computing system is adapted to to create the reference genome index.

13. The system of claim 12, wherein the host computing system is further adapted to determine all <seed, location> tuples in the reference genome sequence to form a plurality of <seed, location> tuples; to sort and eliminate redundant tuples from the plurality of <seed, location> tuples; for each seed, to generate a forward sequence and a reverse complement sequence and determine which of the forward sequence or the reverse complement sequence is lexicographically smaller; for each seed, to hash the lexicographically smaller sequence to produce a hash result; and for each seed, to use the hash result as the hashed seed for the reference genome index.

14. The system of claim 13, wherein the host computing system is further adapted to create a pointer table, each entry of the pointer table comprising a first predetermined number of the most significant bits of the selected hashed seed and a corresponding pointer; and create a candidate alignment location table, each entry of the candidate alignment location table comprising a second predetermined number of the least significant bits of the selected hashed seed and a corresponding candidate alignment location.

15. The system of claim 1, wherein the one or more field programmable gate arrays are further configured to filter the plurality of candidate alignment locations to eliminate any redundant candidate alignment locations.

16. The system of claim 1, wherein the one or more field programmable gate arrays are further configured to perform a Smith-Waterman string matching of the short read with the reference genome sequence to determine the likelihood of the short read matching the reference genome sequence.

17. The system of claim 16, wherein the one or more field programmable gate arrays are further configured to perform a plurality of Smith-Waterman string matching operations in parallel.

18. The system of claim 1, wherein the one or more field programmable gate arrays are further configured to determine the vicinity of the candidate alignment location as a sequence beginning at the start of the candidate alignment location minus a predetermined offset and extending through the end of the candidate alignment location plus a length of the selected short read and the predetermined offset.

19. The system of claim 1, wherein the one or more field programmable gate arrays are further configured to perform the selections, extraction, and determinations in parallel.

20. The system of claim 1, wherein the reference genome sequence is divided into a plurality of reference blocks, each reference block having a size corresponding to a single read from the one or more memory circuits.

21. A system for acceleration of short read mapping to a reference genome sequence for genomic analysis, the system coupled to a host computing system, the system comprising:
one or more memory circuits storing a plurality of short reads, a reference genome sequence, and a reference genome index, each short read comprising a sequence of a plurality of genetic bases, the reference genome index comprising a pointer table and a candidate alignment location table; and
one or more field programmable gate arrays coupled to the one or more memory circuits, the one or more field programmable gate arrays configured to select a short read from the plurality of short reads; to extract a plurality of seeds from the short read, each seed comprising a genetic subsequence of the short read; for each seed of the plurality of seeds, to generate a forward sequence and a reverse complement sequence for the selected seed and determine which of the forward sequence or the reverse complement sequence is lexicographically smaller; to hash the lexicographically smaller sequence to produce a hash result; to use the hash result to access the reference genome index to determine a candidate alignment location in the reference genome sequence to form a plurality of candidate alignment locations; for each candidate alignment location of the plurality of candidate alignment locations, to perform string matching to determine a likelihood of the short read matching the reference genome sequence in the vicinity of the candidate alignment location; and to select a candidate alignment location, of the plurality of candidate alignment locations, having the currently greatest likelihood of the short read matching the reference genome sequence.

* * * * *

SEQUENCE LISTING

```
<160> NUMBER OF SEQ ID NOS: 1

<210> SEQ ID NO 1
<211> LENGTH: 31
<212> TYPE: DNA
<213> ORGANISM: Artificial Sequence
<220> FEATURE:
<223> OTHER INFORMATION: Example for computation
<220> FEATURE:
<221> NAME/KEY: misc_feature
<222> LOCATION: (1)..(31)

<400> SEQUENCE: 1
agggttattt accctactgc gactatctag t                                       31
```